United States Patent
Pandey et al.

(10) Patent No.: US 6,635,763 B2
(45) Date of Patent: Oct. 21, 2003

(54) PROCESS TO PREPARE CLOPIDOGREL

(75) Inventors: Bipin Pandey, Gujarat (IN); Vidya Bhushan Lohray, Gujarat (IN); Braj Bhushan Lohray, Gujarat (IN)

(73) Assignee: Cadila Health Care Limited, Gujarat (IN)

( * ) Notice: Subject to any disclaimer, the term of this patent is extended or adjusted under 35 U.S.C. 154(b) by 0 days.

(21) Appl. No.: 10/054,101

(22) Filed: Oct. 22, 2001

(65) Prior Publication Data

US 2002/0177712 A1 Nov. 28, 2002

(30) Foreign Application Priority Data

Jan. 24, 2001 (IN) ..................... 84/MUM/2001

(51) Int. Cl.$^7$ ............................. C07D 47/04
(52) U.S. Cl. ....................................... 546/114
(58) Field of Search .......................... 549/114

(56) References Cited

U.S. PATENT DOCUMENTS 4,529,596 A    7/1985  Aubert et al. ............... 546/114
4,847,265 A  * 7/1989  Badorc et al. ............... 514/301
6,180,793 B1 * 1/2001  Bakonyi et al. ............. 546/114

OTHER PUBLICATIONS

Burgos et al, J. of Labelled Cpds. and Radiopharmaceuticals, vol. 43, p.891–898 (2000).*

Burgos, et al., "*orhto*–Metalation/Chlorination of Benzoic Acid Derivatives: Preparation of [*benzene*–U–$^{13}$C–*rac*–SR25990C]," *Journal of Labelled Compounds and Radiopharmaceuticals J. Labelled Cpd. Radiopharm.* 43, 891–890 (2000), XP008008850.

March, "Addition to Carbon–Carbon Multiple Bonds," *Advanced Organic Chemistry*, 1992, Wiley & Sons, New York XP–002215119.

Najer et al., "Nitriles, amides, thioamides et acides alpha–phényle alpha–tertioaminoacétiques," *Bull. Soc. Chim. Fr.*, 1958, 1189–92, XP002215118.

* cited by examiner

Primary Examiner—Bernard Dentz
(74) Attorney, Agent, or Firm—Steven J. Moore

(57) ABSTRACT

The present invention relates to a process for the preparation of thieno[3,2-c]pyridine derivatives having pharmacologically significant anti-aggregating and anti-thrombotic properties.

28 Claims, No Drawings

PROCESS TO PREPARE CLOPIDOGREL

FIELD OF THE INVENTION

The present invention relates to a process for the preparation of thieno[3,2-c]pyridine derivatives of general formula (I), in either racemic or optionally active (+) or (−) forms and their salts, wherein X, the substituent on benzene ring represents either a hydrogen or halogen atom such as fluorine, chlorine, bromine or iodine.

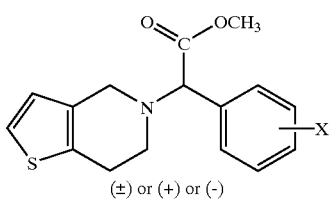

(±) or (+) or (−)

Preferably, X represents 2-chloro.

The present invention also describes a process for preparing the compounds of general formula (II), in either racemic or optically active (+) or (−) forms and their salts, where X, the substituent on benzene ring represents either a hydrogen or halogen atom such as fluorine, chlorine, bromine or iodine.

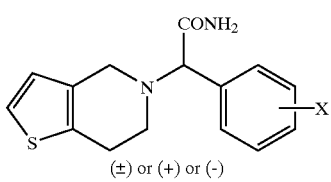

(±) or (+) or (−)

Preferably X represents 2-chloro. These compounds are useful intermediates to prepare compounds of general formula (I).

The compounds represented by formulae (I) and (II) have one asymmetric carbon and hence, to obtain optically active compounds of formula (I) or of formula (II), option available is either to resolve the racemic intermediate/final product or use an optically active intermediate.

BACKGROUND OF THE INVENTION

Thieno[3,2-c]pyridine derivatives disclosed in FR 2,215, 948, FR 2,530,247 and FR 2,612,929, are pharmacologically active and have significant anti-aggregating and anti-thrombotic properties. One such example is 'Clopidogrel', (S)-(+)-(2-chlorophenyl)-(6,7-dihydro-4H-thieno[3,2-c]pyridin-5-yl) acetic acid methyl ester and its pharmaceutically acceptable salts. Later, it was found that the biological activity resides only with (S)-(+)stereoisomer (U.S. Pat. No. 4,847,265). As 'Clopidogrel base' is an oily liquid, in order to prepare a convenient formulation, the base is converted into a pharmaceutically acceptable salt. Suitable salts of 'Clopidogrel base' can be formed with taurocholate, hydrobromide and sulfuric acid.

DESCRIPTION OF THE PRIOR ART

The reported methods to synthesize the compounds of general formula (I) (U.S. Pat. No. 4,529,596, GB 0420706 and GB 0466569), use α-halophenylacetic acid derivatives, which are lacrimatory and irritant in nature. The processes to synthesize such compounds involve multiple steps, and have other drawbacks due to the chemicals/reagents used, which usually are difficult to handle, scale-up and unfavorable from human health as well as environmental point of view. Moreover, overall yields of these processes range from poor to average. Various other synthetic approaches found in literature, involve expensive or hazardous chemicals, which do not significantly improve the yield of the desired product.

Recently, radiolabelled (bezene-U-$^{13}$C) racemic(±)-Clopidogrel has been prepared as a standard for metabolic studies in an overall yield of 7% using orthometalation/chlorination of benzoic acid derivative (*Chem. Abst,* 133:281711, 2000). Various other strategies are disclosed in: WO 98/51681, WO 98/51682, WO 98/51689, WO 99/18110, U.S. Pat. Nos. 4,876,362, 5,036,156, 5,132,435, 5,139,170, 5,204,469 and 6,080,875.

Recently, a new polymorph of Clopidogrel bisulfate (named as form II) has been disclosed in patent application (WO 99/65915), which has a melting point of 176±3° C. It also mentions that the compound disclosed in the earlier US patent (U.S. Pat. No. 4,847,265), had a different melting point of about 184±3° C. (now referred as, form I). It has been shown that both the polymorphs have distinct and characteristic XRD and IR spectrum.

Consequently, the present invention aims to provide an inexpensive and commercially viable process to prepare compounds of formula (I) in good yields.

OBJECTS OF THE INVENTION

The main object of the present invention is to provide a novel process to prepare thieno[3,2-c]pyridine derivatives, represented by the general formula (I), in either racemic or optically active (+) or (−) forms and their salts, wherein X represents either hydrogen or halogen atom such as fluorine, chlorine, bromine or iodine.

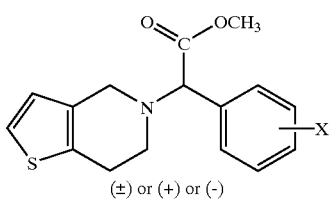

(±) or (+) or (−)

Another the object of the present invention is to provide a novel process to prepare thieno[3,2-c]pyridine derivatives, represented by the general formula (I), in either racemic or optically active (+) or (−) forms and their salts, through a commercially viable route.

A particular object of the present invention is to provide a novel process to manufacture (S)-(+)-(2-chlorophenyl)-(6, 7-dihydro-4H-thieno[3,2-c]pyridin-5-yl)acetic acid methyl ester as bisulfate salt, i.e. Clopidogrel bisulfate, where X is 2-chloro substituent.

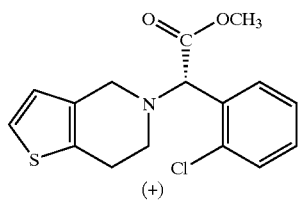

The preferred object of the present invention is to provide a novel process to manufacture Clopidogrel bisulfate, through a commercially viable process.

Another important object of the present invention is to provide a novel process to manufacture polymorph form I of Clopidogrel having melting point 184±3° C., through commercially viable route.

Yet another object of the present invention is to recycle through a novel process the laevoisomer of Clopidogrel or a variable mixture of (+) and (−) stereoisomers to make (+)-Clopidogrel bisulfate.

Another object of the present invention is to provide a process to prepare a compound (2-chlorophenyl)-(6,7-dihydro-4H-thieno[3,2-c]pyrid-5-yl)acetamide of formula (A), either in racemic or as optically active (+) or (−) forms and their salts.

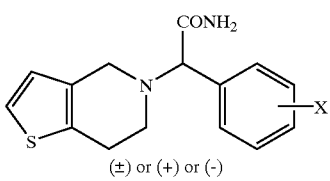

Another object of the present invention is to provide a process for the preparation of a compound of formula (I) where X is 2-chloro, in racemic as well as optically active (+) or (−) forms having suitable chemical and chiral purity and along with their salts. The dextro isomer of compound with formula (II) with suitable purity or its salts, are useful intermediates for the synthesis of (+)-Clopidogrel bisulfate.

Still another object of the present invention is to provide a novel process to convert (R)-(−)-(2-chlorophenyl)-(6,7-dihydro-4H-thieno[3,2-c]pyrid-5-yl)acetamide or its mixture with variable minor amounts of its optical antipode, into almost a 1:1 mixture of (+) and (−) isomer.

It is also an object of the present invention is to provide a process to prepare compound of formula (III), (2-chlorophenyl)-(6,7-dihydro-4H-thieno[3,2-c]pyrid-5-yl) acetic acid, in racemic (±) or in either of the optically active (+) or (−) form, and their salts.

Still another object of the present invention is to provide a novel process to convert (R)-(−)-(2-chlorophenyl)-(6,7-dihydro-4H-thieno[3,2-c]pyrid-5-yl)acetic acid in a mixture to (S)-(+) stereoisomer.

Another object of the present invention is to provide a process for the preparation of a compound of formula (IV), (±)-(2-chlorophenyl)-(6,7-dihydro-4H-thieno[3,2-c]pyrid-5-yl)acetonitrile, and their salts.

Still another object of the present invention is to provide a novel process to convert (R)-(−)-(2-chlorophenyl)-(6,7-dihydro-4H-thieno[3,2-c]pyrid-5-yl)acetonitrile or its mixture with variable minor amounts of its optical antipode, into almost a 1:1 mixture of (+) and (−) isomer.

The process described herein provides a simple and alternative method to prepare compounds of the general formula (I), particularly (S)-(+)Clopidogrel bisulfate, polymorph form I.

SUMMARY OF THE INVENTION

The above and other objects of the present invention are achieved by the process of the present invention by employing compounds of formula (II)

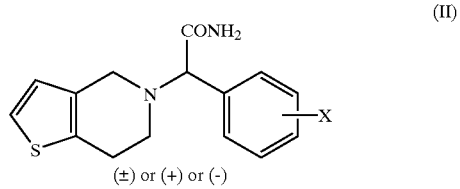

or its salts, in either racemic or optically active (+) or (−) forms, as outlined in Scheme 1.

Optionally, the present invention provides a method to resolve (−)-2-chlorophenyl)-(6,7-dihydro-4H-thieno[3,2-c]pyrid-5-yl)acetamide into optically active (+) or (−) forms, which can be used to prepare (+)-Clopidogrel bisulfate.

Optionally, the present invention provides a method to resolve (±)-2-(2-chlorophenyl)-(6,7-dihydro-4H-thieno[3,2-c]pyrid-5-yl)acetic acid into optically active (+) or (−) forms.

Optionally, the present invention provides a method to resolve (±)-(2-chlorophenyl)-(6,7-dihydro-4H-thieno[3,2-c]pyrid-5-yl)acetonitrile into optically active (+) or (−) forms

DETAILED DESCRIPTION OF THE INVENTION

Accordingly, the present invention provides a process to prepare compounds of formula (I), in either racemic or optically active (+) or (−) forms and their salts, where X represents either hydrogen or a halogen atom such as fluorine, chlorine, bromine or iodine. More particularly, the present invention provides a process to prepare Clopidogrel bisulfate.

The process to prepare compounds of formula (I) or its salts, uses compounds of formula (II)

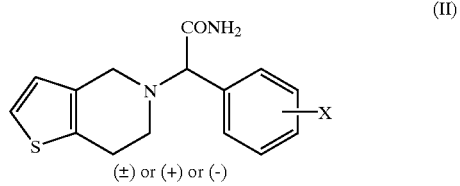

or its salts, in either racemic or optically active (+) or (−) forms, as outlined in Scheme 1.

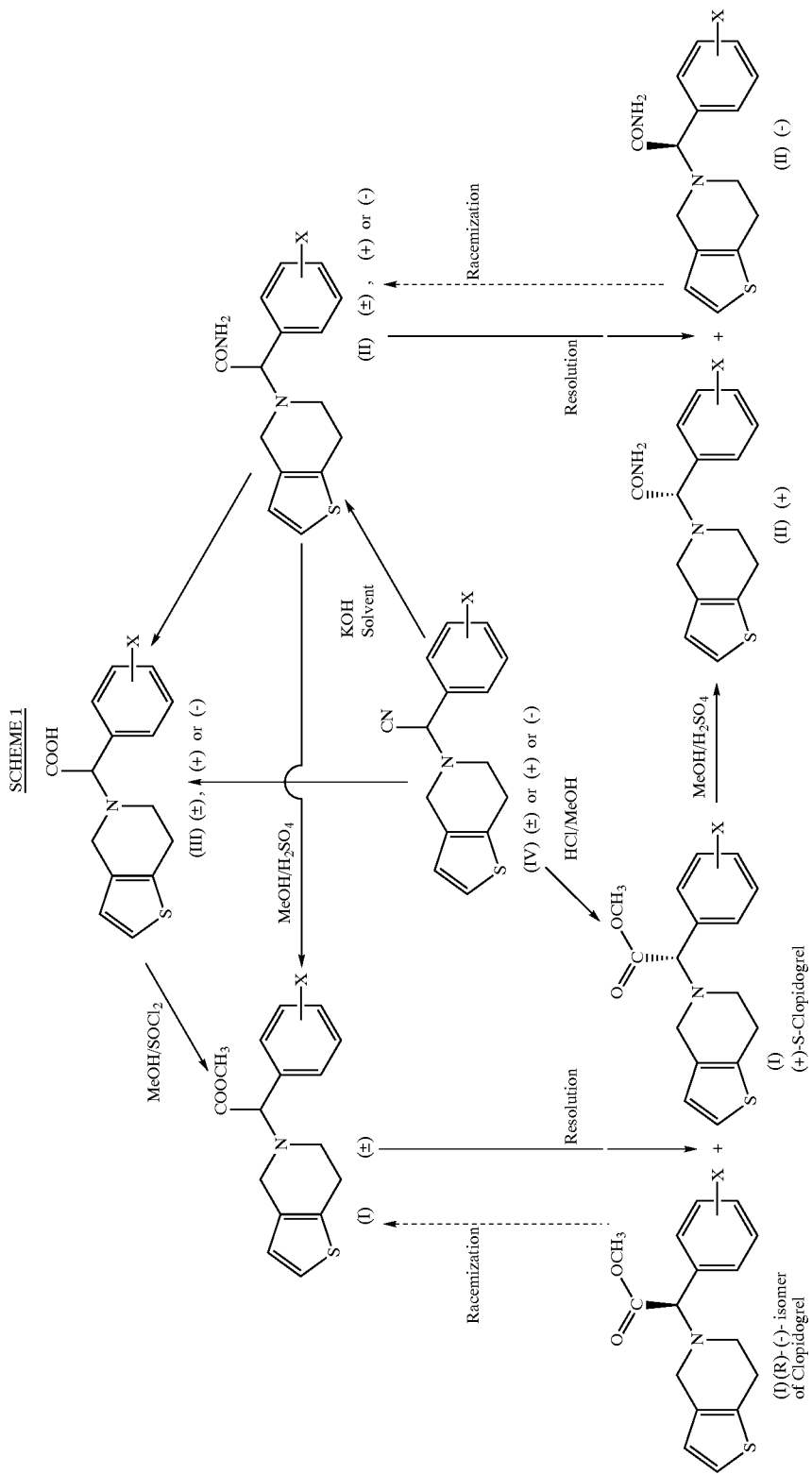
SCHEME 1

Each intermediate in Scheme 1 has one chiral center. Hence, to prepare an optically active product, such as compound represented by formula (I), particularly Clopidogrel and its salt, it is possible to use an optically active intermediate from the first step onwards.

The present invention provides a process for the preparation of compounds of formula (I) and their salts as shown in scheme 1, which comprises:
1. preparing compound of formula (IV), (±)-(2-chlorophenyl)-(6,7-dihydro-4H-thieno[3,2-c]pyrid-5-yl) acetonitrile as described in Scheme 2, i.e. via Strecker reaction;
2. resolving, if desired, the racemic mixture of compound of formula (IV) into its optically active (+) and (−) stereoisomers; and recycling the unwanted stereoisomer into the process by racemization;
3. transforming the compound of formula (IV) in either racemic or optically active (+) or (−) form or its salt, into the compound of formula (II), (±)-(2-chlorophenyl)-(6,7-dihydro-4H-thieno[3,2-c]pyrid-5-yl)acetamide or optically active corresponding (+) or (−) form, based upon starting material used;
4. resolving, if desired, the racemic compound of formula (II)—into its optically active (+) and (−) stereoisomers; and recycling the unwanted stereoisomer into the process by racemization;
5. transforming the compound of formula (II), either in racemic or optically active (+) and (−) form or its salt, into either optically active or racemic compound of formula (I), (±)-(2-chloro phenyl) (6,7-dihydro-4H-thieno[3,2-c]pyrid-5-yl)acetate methyl ester, in racemic or optically active (+) and (−) form and its salt, based upon starting material used;
6. further resolving and/or transforming the racemic/optically active compound of formula (I) into their pharmaceutically acceptable salts and/or, liberating the racemic or optically active compound of formula (I) from its salts.

Alternatively, either of the compounds of formulae (IV) or (II), either racemic or optically active (+) or (−) form can be transformed into corresponding compounds of formula (III); which can then be converted into corresponding compound of formula (I).

The compound of formula (IV) in racemic or optically active (+) or (−) forms can be directly converted into corresponding compound of formula (I).

Optionally, suitable acid addition salts of the intermediates of formula II, III and IV may be used in the above mentioned processes. Suitable acids used may be selected from acetic, benzoic, fumaric, maleic, citric, tartaric, gentisic, methanesulfonic, ethanesulfonic, benzenesulfonic, p-toluenesulfonic, camphor sulfonic, hydrochloric, sulfuric, hydrobromic acids and the like.

Another aspect of the present invention is to provide a process for the preparation of a novel intermediate of formula (IV) and its salts.

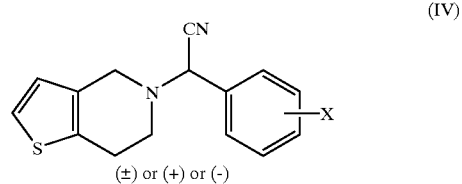

(±) or (+) or (−)

Yet another aspect of the process of invention includes preparation of intermediate described by general formula (IV) and as depicted in the Scheme 2, by Strecker reaction, using a secondary amine (Organic Synthesis Collective Volume III, page no. 275).

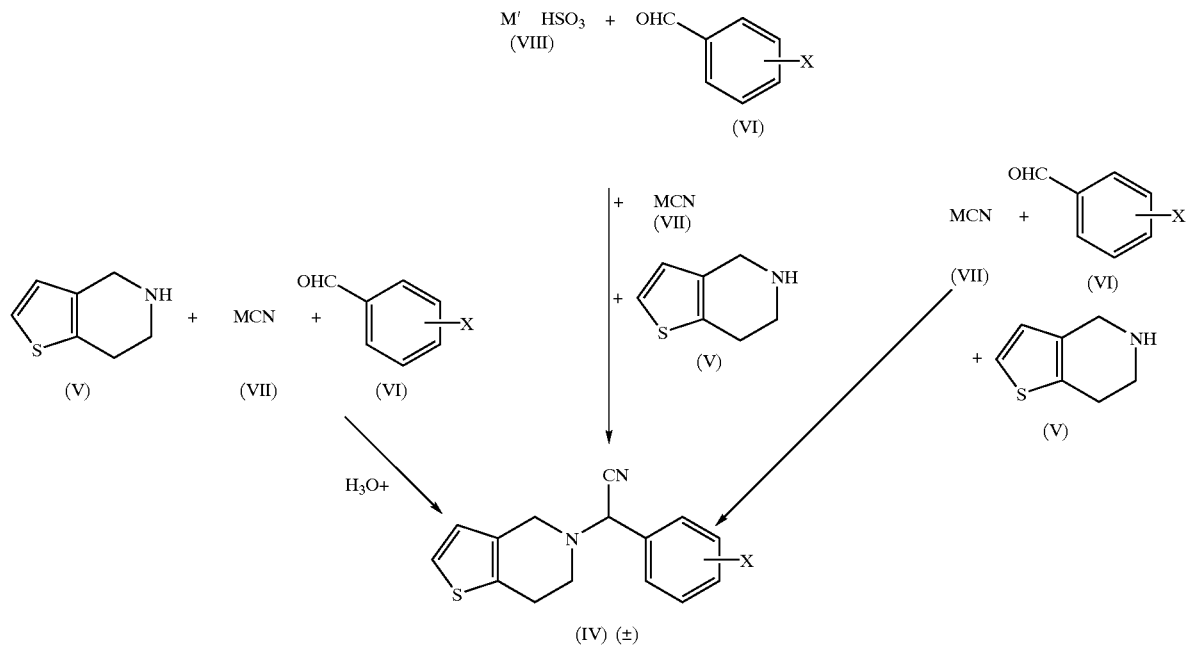

The process to prepare compounds of formula (IV) includes, reacting amine of formula (V) or its salt, with a cyanide derivative of the general formula (VII), wherein M represents either alkali metals such as Na, K, Li, or H, trimethylsilyl (TMS) and the like; with 2-chlorobenzaldehyde of formula (VI). The synthesis of amine or its salt having formula (V) is described in FR 2608607.

The above reaction can be carried out in various ways. A few such methods are outlined in Scheme 2 shown above. Initially, amine of formula (V), or its salt, is reacted with cyanide (VII), wherein M is as defined earlier, followed by addition of 2-chlorobenzaldehyde (VI). Alternatively, 2-chlorobenzaldehyde (VI) is treated with cyanide of formula (VII), wherein M is as defined earlier, and the intermediate cyanohydrin is further reacted with amine of formula (V) or its salt. In an alternative method, 2-chlorobenzaldehyde of formula (VI) is added to hydrogen sulfite derivative of formula (VIII) wherein M' represents Na, K, Li and the like; followed by reaction with cyanide of formula (VII), wherein M is as defined earlier, and finally amine of formula (V) or its salt in an in situ reaction. Irrespective of the variations in the reaction methodology, the yield of resultant intermediate (IV) obtained is comparable.

The preferred method involves, addition of 2-chlorobenzaldehyde of formula (VI) to hydrogen sulfite derivative of formula (VIII). The salt formed is treated with cyanide of formula (VII), and finally with an amine of formula (V) or its salt in presence of suitable reagent and solvents.

Suitable reagents includes acid catalysts, such as glacial acetic acid (Synthesis, 1989, 616–618), hydrochloric acid, sulfuric acid, methanesulfonic acid, trifluoroacetic acid, polyphosphoric acid and the like.

Suitable solvents can be hydrophilic solvents, either protic or aprotic, includes water, $(C_1-C_4)$ alcohol, tetrahydrofuran, dimethyl formamide, DMSO, dioxane, 1,2-dimethoxyethane, acetic acid, propionic acid and the like, or a mixture of solvents thereof. The preferred solvent is a mixture of solvents and water in varying ratio. The more preferred reaction medium includes a mixture containing water and $(C_1-C_4)$ alcohol in a ratio varying between 1:1 and 1:10.

When the reaction is carried out in aprotic or hydrophobic solvent, a phase transfer catalyst and a biphasic solvent system is necessary. Suitable phase transfer catalyst used in such a case may be tetrabutyl ammonium halide, benzyltrimethylammonium halide, and the like.

During the reaction, certain additives may be added. Such suitable additives may be cyclo[(S)-histidine-(S)phenyl alanine] and the like.

The reaction temperature may range from −30° C. to reflux temperature of the solvent(s) used. The preferred temperature ranges from 0° C. to 100° C., and more preferably, from 40° C. to 80° C. However, when HCN (g) (Scheme 2, Intermediate VII, M=H) is used the required temperature is in the range of about −30° C. to −10° C.

This reaction may be carried out in the absence or presence of an inert atmosphere such as $N_2$, He or Ar. The duration of the reaction may vary from 1 hrs to 3 days, more specifically 2 hrs to 2 days.

It is preferable to react a compound of formula (V), hydrogen sulfite derivative (VIII), and cyanide derivative (VII) with respect to 2-chloro benzaldehyde (VI) in the ratio preferably between 1 to 1.2 equivalents. The racemic cyano compound (IV) thus obtained, can be resolved into optically active (+) and (−) forms.

The cyano compound (IV) thus obtained can be converted into corresponding acid of formula (III), amide of formula (II) or acid of formula (I) as shown in Scheme 1 (R. C. Larrock, in "Comprehensive Organic Transformations", John Wiley & Sons, Inc, 1999, 2nd Ed., 815–818 and references therein).

Yet, another aspect of the present invention is to convert these intermediates II and III, into compounds of formula I, as shown in scheme 1. Each of (±), (+) or (−) the isomer of intermediate of formulae II and III, can be converted into the corresponding isomer of compounds of formula I.

The preferred route to obtain the compound of formula (I), involves conversion of either (±), (+) or (−) isomer cyano compound (IV) and its salts, into amide compound of formula (II), in the presence of suitable acids/base reagents in suitable solvents. Later resolving the amide into optically active (+) or (−) form or its salt and the optically active amide is being converted into optically active ester of formula (I) in presence of suitable catalyst and reagent.

The reaction to convert cyano compound of formula (IV) into amide compound of formula (II) may be carried out in presence of reagents, which include acid or a base. Suitable acids which may be used are, acetic acid, p-toluenesulfonic acid, trifluoroacetic acid, chloroacetic acid and the like or anhydrous alcoholic or aqueous solution of mineral acids such as sulfuric acid, HCl, HBr and the like. A base is preferred whenever the starting material is a racemic mixture. Suitable base which may be used are lithium hydroxide, sodium hydroxide, potassium hydroxide, potassium tert-butoxide, or mixtures thereof, preferably alkali metal hydroxides. Along with alkali metal hydroxides, excess of hydrogen peroxides or metal peroxides may also be used in the above reaction. Suitable solvent/s for the above reaction may be aqueous, polar or protic solvents such as water, $(C_1-C_4)$alcohol, acetone, acetic acid, dimethyl formamide, THF, DMSO, dioxane, DME and the like or mixtures thereof; preferably solvent consists of water, methanol or tert-BuOH or mixture of these solvents, in a ratio varying between 1:1 to 1:10.

The temperature ranges from 20° C. to 250° C., preferably, from 50° C. to 150° C. The reagents used in the above process can be in the range from 0.01 to 1.2 moles equivalents. The reaction may be carried out in the absence or presence of an inert atmosphere such as $N_2$, He or Ar. The reactions under the basic conditions are preferably under inert atmosphere. The duration of reaction may range from ½ hr to 5 days, preferably from 2 hrs to 2 days.

The amide of formula (II), in either racemic or optically active (+) or (−) form, or their salt, can be converted to corresponding methyl ester of formula (I), in presence of at least one equivalent of methanol and acid, in suitable solvent.

Suitable acids which can be used include acetic acid, polyphosphoric acid, p-toluenesulfonic acid, trifluoroacetic acid, chloroacetic acid, or mineral acids, which includes, sulfuric acid, HCl, HBr and the like, which could be in different forms like acid dissolved in alcohol, anhydrous acids dissolved or saturated in alcohol and alcohol used may be methanol. The preferable acid is concentrated sulfuric acid in the 1 to 50 equivalent ratio. Suitable solvents for the above transformation may be polar or protic solvent such as hydrophilic solvents including methanol, acetone, acetic acid, THF, DMSO, dioxane, DME and the like or mixtures thereof. The preferable solvent consists of methanol at least in one equivalent and may be in large excess such that it acts as a solvent. Sometimes inert cosolvent, such as toluene, xylene etc. can also be used.

The temperature ranges from 20° C. to 250° C., preferably from 50° C. to 150° C. The reaction may be carried out in the absence or presence of an inert atmosphere such as $N_2$, He or Ar. The duration of reaction may range from 3 hrs to 5 days, preferably from 4 hrs to 2 days.

It is possible to convert compound of formula (IV) in either racemic or optically active (+) or (−) form or its salt is converted into the corresponding acetic acid derivative of formula (III) in presence of suitable solvent and reagent. Suitable solvent/s may be aqueous or alcoholic in nature. Suitable reagents for the above reaction include acids as well as bases.

It is also possible to convert the cyano compound of formula (IV) in either racemic or optically active (+) or (−) form or its salts, directly into methyl ester of formula (I), in presence of at least one equivalent of acid and at least one equivalent of methanol in suitable solvents according to methods known in the literature.

The acid of formula (III) in either racemic or optically active (+) or (−) form or its salts can be converted into corresponding methyl ester of formula (I), in presence of suitable reagent in suitable solvents and at least one equivalent of methanol.

Suitable reagent which can be used include, thionyl chloride, acid chlorides such as pivaloyl chloride, alkylchloroformates like ethyl or methyl chloroformates and other such reagents which activate the COOH group, in a 1:1 equivalent ratio. Suitable solvent for the above transformations may be polar or protic solvent such as, methanol, acetone, dimethylformamide, THF, DMSO, dichloromethane, dichloroethane, dioxane, DME and the like or mixtures thereof. The preferable solvent consists of methanol in at least one equivalent and may be in large excess such that it acts as a solvent. The temperature ranges from 20° C. to 250° C., preferably from 50° C. to 150° C.

The reagents used in above process may range from 0.01 moles to equimolar ratios. The reaction may be carried out in the absence or presence of an inert atmosphere such as $N_2$, He or Ar. The duration of reaction may range from 3 hours to 5 days, preferably from 3 hr to 2 days.

This manufacturing process to prepare the compounds of general formula (I) as shown in scheme 1, has following advantages:

1) It requires less number of steps to prepare the compounds of the formula (I).
2) Simple readily available reagents/chemicals are used.
3) Milder reaction conditions are employed in various steps.
4) It is possible to get chiral/optically active intermediates at every stage (I, II, III or IV)
5) It is possible to racemize the unwanted isomers thereby enhancing efficiency and reducing environmental load.
6) The above factors contribute to improve cost effectiveness of the process described herein.

The compounds of the formulae (I), (II), (III) and (IV) can be resolved by various methods to get optically active compounds of the formulae (I), (II), (III) and (IV), which can give Clopidogrel of desired stereochemistry (R. A. Sheldon, in "Chirotechnology", Marcel Dekker, Inc. NY, Basel, 1993, 173–204 and references therein; A. N. Collins, G. N. Sheldrack and J Crosby, in "Chirality in Industry II", John Wiley & Sons, Inc, 1997, 81–98 and references therein; E. L. Eliel and S. H. Wilen, in "Stereochemistry of Organic Compound", John Wiley & Sons, Inc, 1999, 297–464 and references therein).

The process of resolution comprises of dissolving the racemic mixture (of formulae I, II, III or IV) in suitable solvent and addition of a suitable chiral reagent. Optionally the medium may contain water about <5%. Suitable solvent is selected on the basis whether the diastereomeric salt precipitates out differently. The separation of diastereomeric salt may result either spontaneously or by addition of cosolvent or salting out or evaporation of the solvent or addition of a cosolvent. Alternatively, the separation may result simply by stirring at a suitable temperature in a solvent(s) until one of the salts preferentially precipitate out. Purification of diastereomeric salt is possible by refluxing in a suitable solvent. The free base is liberated from its salt using a suitable base reagent. The diastereomeric salt is dissolved or suspended in a mixture of water and organic solvent and is neutralized with a base under stirring. Free base is obtained after separation of aqueous layer and evaporation of the organic solvent.

The solvents used during the resolution can include solvents or mixtures thereof such as ($C_1$–$C_4$) alcohol, ($C_1$–$C_4$)ketone, dimethylformamide, ethyl acetate, methyl acetate, methyl ethyl ketone, acetonitrile, propionitrile, THF, dioxane and the like; the solvent used optionally may contain water up to 5%, but presence of water or its amount is not critical. Suitable temperature range for the resolution includes temperature from 0° C. to reflux temperature of the solvent used, preferably 0° C. to 80° C. The acid chiral reagents, which can be used to form a diastereomeric salt, include tartaric acid, mandelic acid, lactic acid, camphorsulfonic acid, lactic acid, maleic acid, amino acids and the like.

By repeated crystallization from a suitable solvent, the precipitated salt is enriched in the salt of dextrorotatory isomer of the desired diastereomer to yield a product of constant optical rotation.

Suitable base reagent for the hydrolysis of diastereomeric salt includes sodium carbonate, potassium carbonate, sodium hydrogen carbonate and potassium hydrogen carbonate in aqueous media at temperatures varying between 5° C. to 25° C.

Finally, the desired salt of compound of formula (II), (III), or (IV); or pharmaceutically acceptable salt of compound of formula (I) can be formed from the corresponding stereoisomer and a suitable acid. The optically pure (S)-(+) compound of formula (I), is converted into its bisulfate salt using sulfuric acid 70% to 98%, in an appropriate solvent at suitable temperature to afford (+)-Clopidogrel bisufate, polymorph I as desired.

Alternatively, the diastereomers formed may be separated by conventional methods of purification such as fractional crystallization, column chromatography and the like followed by cleavage of salt to give product of desired stereochemistry. It is preferable to use, such a chiral agent, which can selectively form diastereoisomer with either R or S stereoisomer of intermediate I, II, III or IV. The chiral reagent used may be in 0.5 to 1.1 molar ratio.

Determination of the enantiomeric purity of the (+)-dextrorotatory and (−)-laevorotatory enantiomers may be carried through proton NMR spectroscopy with the addition of a chiral rare earth reagents (shift reagents) or by HPLC using a chiral stationary phase as well as through measurement of optical rotation.

The absolute stereochemistry of the diastereomeric salt of II, III or IV compounds may be determined using conventional methods, such as X-ray crystallography. The absolute stereochemistry of chiral compounds can also be determined by comparing it with reference standards known in literature.

The pharmaceutically acceptable mineral and organic acid salts of optically active enantiomers of Clopidogrel are prepared using various acidic salts, which forms a part of this invention but are not limited to hydrogen sulfates, hydrohalides, taurocholates and the like.

More specifically the present process of invention results in Clopidogrel bisulfate of melting point 184±3° C., which is characteristic of Clopidogrel bisulfate form I. Alternatively, Clopidogrel bisulfate form II can also be prepared by known method (WO 99/65915, FR 98 07464).

The process of this invention also includes the process to recycle the unwanted stereoisomer through racemization. The conditions for racemization of all the intermediates of general formula II, III or IV as well as final product I, involves the similar solvent and catalyst in equimolar quantities. Suitable catalyst is generally a base such as LDA (Lithium diisopropylamide), KOH, NaOH, $K^+$-t-BuO$^-$, NaOMe, NaH, KH and the like. Suitable solvent used during the resolution can include solvents or mixtures thereof such as ($C_1$–$C_4$) alcohol, ($C_1$–$C_4$)ketone, ethyl acetate, methyl acetate, methyl ethyl ketone, THF, dioxane and the like; the solvent used optionally may contain water up to 5%. Suitable temperature range for the resolution includes temperature from 0° C. to reflux temperature of the solvent used, preferably 0° to 80° C.

The process described in the present invention is demonstrated in the examples illustrated below. These examples are provided as illustration only and therefore should not be construed as limitation to the scope of the invention.

EXAMPLE 1

(±)-(2-chlorophenyl)-(6,7-dihydro-4H-thieno[3,2-c] pyrid-5-yl)acetonitrile (IV)

To a solution of 8.98 g (86.33 mmole) sodium bisulfite in water (27 mL), o-chlorobenzaldehyde 12.4 g (86.33 mmole) was added resulting in a white precipitate. To the precipitate, 15 g (0.107 moles) of 6,7-dihydro-4H-thieno[3,2-c]pyridine was added, followed by addition of 4.4 g (89.7 mmoles) NaCN (dissolved in 15 mL water). The reaction mixture was heated at 40–50° C. for 6 hrs and was quenched by pouring in water (50 mL). The mixture was extracted with 2×100 mL of ethyl acetate. The organic layer was dried over anhydrous sodium sulfate and the solvent was removed under reduced pressure. The yield of the title product is 24 g (97%).

The product obtained was characterized using IR spectrum, Mass, $^{13}$C-NMR and $^1$H-NMR, which are as given below:

| | |
|---|---|
| IR spectrum (cm$^{-1}$) | 2227(w, CN group) |
| Mass spectrum (m/z) | 289.1(M + H)$^+$ |
| $^{13}$C-NMR (CDCl$_3$) | δ136.46, 132.78, 132.38, 130.69, 130.46, 130.38, 129.90, 126.73, 124.96, 123.01, 115.09, 59.12, 49.30, 47.66, 25.47. |
| $^1$H-NMR (CDCl$_3$) | δ7.2–7.7(4H, m), 7.0(1H, d), 6.69(1H, d), 5.32(1H, s), 3.78(1H, d), 3.65(1H, d), 2.8–δ3.0(4H, m). |

EXAMPLE-2

(±)-(2-chlorophenyl)-(6,7-dihydro-4H-thieno[3,2-c] pyrid-5-yl)acetonitrile (IV)

140.5 g (1 mol) of o-chlorobenzaldehyde and 65 g of (1.01 mol) KCN was added to 3.5 L of methanol. 139.05 g (1 mol) of 6,7-dihydro-4H-thieno[3,2-c]pyridine and 190 mL of glacial acetic acid was added to the reaction mixture, which was heated at 60° C. for 20 hrs with stirring. After 8 hrs, precipitate begins to appear and then the reaction mixture was poured in water and extracted with (2×25 mL) ethyl acetate. The solvent was removed under reduced pressure and the residue purified as described in Example 1. The yield of product was 187 g (65%), having melting point=123–124° C.

The product obtained was characterized using IR spectrum, Mass, $^{13}$C-NMR and $^1$H-NMR and was found to be identical to the product obtained in example 1.

EXAMPLE-3

(±)-(2-chlorophenyl)-(6,7-dihydro-4H-thieno[3,2-c] pyrid-5-yl)acetonitrile (IV)

27.6 g (266 mmol) of sodium bisulfite was dissolved in 100 mL water, and 38.2 g (271 mmol) o-chlorobenzaldehyde was added after dissolving in 100 mL methanol. A thick white slurry results, which was heated at 60° C. for 1 hour, followed by addition of, 36.97 g (266 mmol) of 6,7-dihydro-4H-thieno[3,2-c]pyridine at 40° C. and was stirred for 2 hrs. To this reaction, 17.29 g (266 mmol) of KCN dissolved in 50 mL water was added carefully and heating was continued at 40° C. for 5–6 hrs, giving white precipitate. The reaction mixture was worked as described in Example 1 and the yield obtained was 54.6 g (72%).

The product obtained was characterized using IR spectrum, Mass, $^{13}$C-NMR and $^1$H-NMR and was found out to be identical to the product obtained in example 1.

EXAMPLE-4

(±)-(2-chlorophenyl)-(6,7-dihydro-4H-thieno[3,2-c] pyrid-5-yl)acetonitrile (IV)

4.5 g (25.64 mmol) 6,7-dihydro-4H-thieno[3,2-c]-5-pyridinium hydrochloride was added (at 10° C.) to solution of potassium cyanide 1.95 g (30 mmol) in 2 mL of ice-cold water, and was followed by dropwise addition of 5 mL concentrated hydrochloric acid at 0° C. After addition of HCl, 3.3 g (23.47 mmol) o-chlorobenzaldehyde dissolved in 50 mL methanol was added dropwise. Later the reaction mixture was kept at room temperature for 3 days and afterwards at 50° C. for 3 hrs. The pH was adjusted to 7.5–8.0 by dropwise addition of NH$_4$OH and the product was extracted with ethyl acetate (2×50 mL). The solvent was dried over sodium sulfate and evaporated under reduced pressure. The amount of product obtained was 1.67 g (18%) with melting point=122–124° C.

The product obtained was characterized using IR spectrum, Mass, $^{13}$C-NMR and $^1$H-NMR and was found to be identical to the product obtained in example 1.

EXAMPLE 5

(±)-(2-chlorophenyl)-(6,7-dihydro-4H-thieno[3,2-c] pyrid-5-yl)acetonitrile (IV)

6.25 g (44.46 mmol) o-chlorobenzaldehyde was dissolved in 60 mL of toluene. To the same flask, 10 mL glacial acetic acid and 1.24 g (4.343 mmol) cyclo[(S)histidine-(S)phenyl alanine] were added, and the temperature was lowered to −25° C. This was followed by addition of 7 g (50.35 mmol) 6,7-dihydro-4H-thieno[3,2-c]pyridine and the reaction flask was purged with HCN gas (at the rate of 30 bubbles/min) at −25° C. for 6 hrs and later was stirred at 31° C. for 2 days. The solvent was removed under vacuum, the residue was purified as mentioned in example 1. The amount of product obtained was 5.5 g (43%) with melting point=124–125° C.

The product obtained was characterized using IR spectrum, Mass, $^{13}$C-NMR and $^1$H-NMR and was found to be identical to the product obtained in example 1.

EXAMPLE 6

(±)-(2-chlorophenyl)-(6,7-dihydro-4H-thieno[3,2-c]pyrid-5-yl)acetonitrile (IV)

As described in Example 5, the adduct was formed between 104.3 g (1 mol) sodium bisulfite and 144.39 g (1.02 mol) o-chlorobenzaldehyde, to which 150 g (1.078 mol) 6,7-dihydro-4H-thieno[3,2-c]pyridine was added at 31° C. to and stirred for 1 hr. 102 g TMS-CN was added dropwise and temperature was maintained at 31° C. for 6 hrs, resulting in a white product, which was isolated and purified according to the procedure in example 1. The yield obtained was 30 g (10%) having melting point about 123–124° C.

The product obtained was characterized using IR spectrum, Mass, $^{13}$C-NMR and $^1$H-NMR and was found to be identical to the product obtained in example 1.

EXAMPLE 7

(±)-(2-chlorophenyl)-(6,7-dihydro-4H-thieno[3,2-c]pyrid-5-yl)acetonitrile (IV)

To 19.5 g (250 mmol) KCN dissolved in water (20 mL) and 43 g (250 mmol) 6,7-dihydro-4H-thieno[3,2-c]pyridine was added, followed by dropwise addition of 50 ml concentrated hydrochloric acid. After the addition was complete, a solution of 33 g (230 mmol) o-chlorobenzaldehyde in 100 mL methanol was added dropwise and stirred for 8 hrs at 31° C. The pH of the reaction mixture was adjusted to 7.5–8.0 using NH$_4$OH and the product was extracted with ethyl acetate (2×500 mL) and washed with water (2×500 mL), brine (500 mL) and was dried over sodium sulfate. The solvent was evaporated under reduced pressure to give of 50 g (74%) the product with melting point of about 123–125° C.

The product obtained was characterized using IR spectrum, Mass, $^{13}$C-NMR and $^1$H-NMR and was found to be identical to the product obtained in example 1.

EXAMPLE 8

(±)-2-chlorophenyl)-(6,7-dihydro-4H-thieno[3,2-c]pyrid-5-yl)acetonitrile (IV)

To the solution of 35.5 g (342 mmol) sodium bisulfite in 35 mL water, 49.1 g (349 mmol) of o-chloro benzaldehyde was added dropwise, whereupon solid adduct forms instantaneously. To this 50 g (284.9 mmol) 6,7-dihydro-4H-thieno[3,2-c]pyridine hydrochloride was added and refluxed for 5 hrs. The usual workup and purification gave 40 g (40%) of the product.

The product obtained was characterized using IR spectrum, Mass, $^{13}$C-NMR and $^1$H-NMR. The product obtained was found to be identical to the product obtained in example 1.

EXAMPLE 9

(±)-(2-chlorophenyl)-(6,7-dihydro-4H-thieno[3,2-c]pyrid-5-yl)acetonitrile (IV)

123.83 g (880 mmol) o-chlorobenzaldehyde and 44 g (897 mmol) sodium cyanide were added to in 100 mL of methanol and water (1:1) mixture. To this 150 g (1070 mmol) 6,7-dihydro-4H-thieno[3,2-c]pyridine was added, followed by the addition of 10 mL concentrated hydrochloric acid and was stirred for 2 days at 31° C. temperature. The pH of reaction mixture was adjusted to 7.5–8.0 using NH$_4$OH. The product was extracted with ethyl acetate (2×50 mL) and washed with water (2×50 mL), brine (50 mL) and was dried over sodium sulfate, and isolated as given in Example 1. The amount of white solid product obtained was 33 g (13%), which was characterized as usual.

EXAMPLE 10

(±)-(2-chlorophenyl)-(6,7-dihydro-4H-thieno[3,2-c]pyrid-5-yl)acetamide (II)

48 g (0.166 mol) (was(2-chlorophenyl)-(6,7-dihydro-4H-thieno[3,2-c]pyrid-5-yl)acetonitrile was suspended in 240 ml t-BuOH, and add 18.26 g (0.332 mol) of KOH was added in one lot with stirring. The reaction mixture was refluxed at 80–82° C. for 3 hr., then cooled to 30° C., 240 mL of water was added and stirred for 20 min. The lower aqueous layer was separated and fresh 720 mL chilled water (5–10° C.) was added slowly in 15 min. The product was extracted with ethyl acetate (2×50 mL) and washed with water (2×50 mL), brine (50 mL) and it was dried over sodium sulfate, followed by isolation by evaporating the solvent under reduced pressure. On treatment with hexane solid was obtained. The yield of product was 48 g (94%).

The product obtained was characterized using IR spectrum, Mass, $^{13}$C-NMR and $^1$H-NMR, which are as given below;

| | |
|---|---|
| IR spectrum (cm$^{-1}$) | 1656(s, C = O group), 2333.7(N – H) |
| Mass spectrum (m/z) | 307.2(M + H)$^+$ |
| $^{13}$C-NMR (CDCl$_3$) | δ173.82, 135.32, 133.42, 133, 130.27, 129.99, 129.4, 126.98, 125.18, 122.98, 69.12, 50.77, 49.10, 25.82. |
| $^1$H-NMR (CDCl$_3$) | δ7.4–7.5(4H, m), 7.24(1H, d), 7.0(1H, s), 6.66(1H, d), 6.0(1H, s), 4.88(1H, d), 3.61(2H, q), 2.88(4H, m). |
| Melting point | 125–127° C. |

EXAMPLE 11

(±)-(2-chlorophenyl)-(6,7-dihydro-4H-thieno[3,2-c]pyrid-5-yl)acetamide (II)

100 mg (0.3466 mmole) (±)-(2-chlorophenyl)-(6,7-dihydro-4H-thieno[3,2-c]pyrid-5-yl) acetonitrile of formula (IV) prepared according to Example 1–9, was dissolved in the 5 mL HCl and 1 mL trifluoroacetic acid and 5 mL t-butanol was added and refluxed for 4 hrs. After the reaction was complete, the product was isolated as mentioned in example 11. The yield of the product was 40 mg (38%).

The product obtained was characterized using IR spectrum, Mass, $^{13}$C-NMR and $^1$H-NMR and was found to be identical to the product obtained in example 10.

EXAMPLE 12

(±)-(2-chlorophenyl)-(6,7-dihydro-4H-thieno[3,2-c]pyrid-5-yl)acetamide (II)

In 100 mg (0.346 mmole) (±)-(2-chlorophenyl)-(6,7-dihydro-4H-thieno[3,2-c]pyrid-5-yl) acetonitrile of formula (IV) (prepared according to Example 1 to 9, 5 mL formic acid and 5 mL concentrated hydrochloric acid was added and the reaction mixture was stirred for 48 hrs at 25–30° C., and later refluxed at approx. 100° C. for 6 hrs and was stirred for 8 days at 25–30° C. After completion of reaction, the reaction mixture was worked up as mentioned in Example 10. The yield of the product was 50 mg (47%).

The product obtained was characterized using IR spectrum, Mass, $^{13}$C-NMR and $^1$H-NMR. The product obtained was identical to the product obtained in example 10.

EXAMPLE 13

(±)-(2-chlorophenyl)-(6,7-dihydro-4H-thieno[3,2-c] pyrid-5-yl)acetamide (II)

200 mg (0.694 mmole) (±)-(2-chlorophenyl)-(6,7-dihydro-4H-thieno[3,2-c]pyrid-5-yl)acetonitrile of formula (IV) prepared according to Example 1–9, was added to 5 ml HBr and 5 ml $H_2O$ and was stirred for 72 hrs at room temperature. The reaction mixture was then refluxed for 11 hrs at 100° C. and the product was isolated as mentioned in example 10. Yield of the product was 50 mg (47%).

The product was characterized using IR spectrum, Mass, $^{13}$C-NMR and $^1$H-NMR and was found to be identical to the product obtained in example 10.

EXAMPLE 14

(±)-(2-chlorophenyl)-(6,7-dihydro-4H-thieno[3,2-c] pyrid-5-yl)acetamide (II)

1 g (3.47 mmole) (±)-(2-chlorophenyl)-(6,7-dihydro-4H-thieno[3,2-c]pyrid-5-yl)acetonitrile, was dissolved in 5 mL $H_2SO_4$(50%). To the reaction mixture 0.405 g anhydrous NaCl was added and reflux the reaction at for 2–3 hrs. At the end of reaction, the product was isolated as described in Example 10. The yield of the product was 600 mg (57%).

The product was characterized using IR spectrum, Mass, $^{13}$C-NMR and $^1$H-NMR and was found to be identical to the product obtained in example 10.

EXAMPLE 15

(±)-(2-chlorophenyl)-(6,7-dihydro-4H-thieno[3,2-c] pyrid-5-yl)acetamide (II)

1 g (3.47 mmole) (±)-(2-chlorophenyl)-(6,7-dihydro-4H-thieno[3,2-c]pyrid-5-yl)acetonitrile was dissolved in the 5 g (5 mmol) $HClO_4$ and 10 mL $H_2O$ was added to the reaction mixture. The reaction mixture was refluxed at 105° C. for 7 hrs and later stirred at room temperature for 12 hrs. The pH was raised until 10–12, using 10% w/v NaOH solution and later extracted with 50 mL dichloromethane. The organic layer was isolated, and washed with water and evaporated under reduced pressure. The residue was treated with hexane to give 50 mg (47% yield) solid, having melting point 125–127° C.

The product obtained was characterized using IR spectrum, Mass, $^{13}$C-NMR and $^1$H-NMR and was found to be identical to the product obtained in example 10.

EXAMPLE 16

(±)-(2-chlorophenyl)-(6,7-dihydro-4H-thieno[3,2-c] pyrid-5-yl)acetamide (II)

1 g (3.47 mmol) of (±)-(2-chlorophenyl)-(6,7-dihydro-4H-thieno[3,2-c]pyrid-5-yl)acetonitrile was suspended in 10 mL t-BuOH, and 277 mg (6.925 mmole) crushed NaOH was dumped under stirring. The reaction mixture was refluxed at 80–82° C. for 4 hrs, followed by cooling to room temperature. The product was isolated by extraction with ethyl acetate. The organic extract was evaporated, and oily material left behind upon hexane treatment yields 400 mg solid (38%).

The product obtained was characterized using IR spectrum, Mass, $^{13}$C-NMR and $^1$H-NMR and was found to be identical to the product obtained in example 10.

EXAMPLE 17

(±)-(2-chlorophenyl)-(6,7-dihydro-4H-thieno[3,2-c] pyrid-5-yl)acetamide (II)

3 g (0.01 mol) (±)-(2-chlorophenyl)-(6,7-dihydro-4H-thieno[3,2-c]pyrid-5-yl)acetonitrile was suspended in 50 mL acetone. To this solution 1 g (0.023 mol) NaOH dissolved in 10 mL water was added, followed by 5 mL $H_2O_2$ (0.05 mol, 30% w/v) in one lot and was refluxed for 3 hrs. The reaction mixture was cooled to room temperature and 5 mL $H_2O_2$ (0.05 mol, 30% w/v) was added again and stirred for 12 hrs. The product was isolated by addition of excess water and extracted with 1 L ethyl acetate. The organic extract was evaporated to give 2.8 g crude oily material, which after treatment with hexane, yields 1 g solid (31%).

The product obtained was characterized using IR spectrum, Mass, $^{13}$C-NMR and $^1$H-NMR and was found to be identical to the product obtained in example 10.

EXAMPLE 18

(±)-(2-chlorophenyl)-(6,7-dihydro-4H-thieno[3,2-c] pyrid-5-yl)acetamide (II)

To 10 g (0.0346 mol) (±)-(2-chlorophenyl)-(6,7-dihydro-4H-thieno[3,2-c]pyrid-5-yl)acetonitrile suspended in 30 ml isopropyl alcohol, 3.9 g (0.0589 mol) crushed KOH (85%) was added slowly and the mixture was warmed, and 120 ml water was added. The pH of aqueous layer was brought to 7 using dilute hydrochloric acid. The white solid precipitate was filtered and washed with 100 mL water. The yield of product was 9 g (85%) with melting point: 122° C.

The product obtained was characterized using IR spectrum, Mass, $^{13}$C-NMR and $^1$H-NMR and was found to be identical to the product obtained in example 10.

EXAMPLE 19

(±)-(2-chlorophenyl)-(6,7-dihydro-4H-thieno[3,2-c] pyrid-5-yl)acetamide Hydrogen Sulfate Salt (II)

2 g (6.48 mole) of (±)-(2-chlorophenyl)-(6,7-dihydro-4H-thieno[3,2-c]pyrid-5-yl)acetamide of formula (IV), was dissolved in 10 mL acetone. To the reaction mixture 1 mL of sulfuric acid was added and was stirred for 0.5 hr. Later 5 mL of diethyl ether was added and stirred overnight at room temperature to obtain a salt. The salt 2 g (76%) was isolated by filtration and washed with acetone.

| Melting point | 199.1° C. |
|---|---|
| IR spectrum | 1682.8, 3116(cm$^{-1}$). |

EXAMPLE 20

(±)-(2-chlorophenyl)-(6,7-dihydro-4H-thieno[3,2-c] pyrid-5-yl)acetic Acid (III)

To 100 mg (0.3466 mmole) (±)-(2-chlorophenyl)-(6,7-dihydro-4H-thieno[3,2-c]pyrid-5-yl) acetonitrile was dissolved in 2 mL t-butanol and add 1.5 mL HCl was added. The reaction mixture was refluxed for 9 hrs at 100° C. In the end, after the completion of reaction, water was added and pH was brought to 4 with 10% KOH solution. The product was extracted with 5 mL dichloromethane and proceeded as given in the earlier example. The yield was 40 mg (38%).

The product obtained was characterized using IR spectrum, Mass, $^{13}$C-NMR and $^1$H-NMR, which are as given below;

| IR spectrum (cm$^{-1}$) | 1637.5(s, C = O group), 3399.3(O – H) |
|---|---|
| Mass peaks (m/z) | 308.1(M + H)$^+$ |
| $^1$H-NMR (δ ppm) | δ7.22–7.89(4H, m), δ7.11–7.12(1H, d), δ6.61–6.63(1H, d), δ3.57–3.67, (2H, d), δ4.13(2H, s), δ3.32–3.42(2H, s). |

EXAMPLE 21

(±)-(2-chlorophenyl)-(6,7-dihydro-4H-thieno[3,2-c]pyrid-5-yl)acetic Acid (III)

5 g (17.33 mmole) (±)-(2-chlorophenyl)-(6,7-dihydro-4H-thieno[3,2-c]pyrid-5-yl)acetonitrile was added to 100 mL HCl and the mixture was stirred for 2 days and later refluxed for 15 hrs. in the end the reaction mixture was dumped in water, and the pH was raised to 4 using 10% KOH. The product was extracted with 2 L dichloromethane, washed with water, and the organic layer was evaporated to obtain the residue. Usual purification of the residue gave 2 g of solid (38%).

The product obtained was characterized using IR spectrum, Mass, $^{13}$C-NMR and $^1$H-NMR. The product obtained was found identical to the product obtained in example 20.

EXAMPLE 22

(±)-Methyl (2-chlorophenyl)-(6,7-dihydro-4H-thieno[3,2-c]pyrid-5-yl)acetate (I)

Mix 10 g (32.62 mmole) (±)-(2-chlorophenyl)-(6,7-dihydro-4H-thieno[3,2-c]pyrid-5-yl) acetamide (prepared according to example 15), with 19.8 g (161.7 mmole) DMFDMA (Dimethyl formamide dimethylacetal) in 100 mL methanol. The mixture was refluxed at 70° C. for 14 hr. Later the reaction mixture was quenched in water and extracted with ethyl acetate. The organic extract was evaporated under reduced pressure to give 5 g of oily product (48%). This oil was used without any further treatment to prepare salts of ester (I).

EXAMPLE 23

(±)-Methyl (2-chlorophenyl)-(6,7-dihydro-4H-thieno[3,2-]pyrid-5-yl)acetate (I)

15 g (0.0490 mol) of (±)-(2-chlorophenyl)-(6,7-dihydro-4H-thieno[3,2-c]pyrid-5-yl)acetamide, was dissolved in 105 mL methanol, with stirring. To the above solution, 45 mL (0.823 mol) of concentrated sulfuric acid (98%) was added dropwise at room temperature and over a period of 1.5 hour. Later the reaction mixture was refluxed at 80° C. for 26 hour, followed by distillation of methanol. To the residue left behind, 200 mL ethyl acetate was added at temperature between 0° C. to 5° C. along with stirring. After the addition 99 g (1.764 mol) KOH dissolved in 300 mL water was added to the reaction and was stirred for 0.5 hour. Finally, the reaction mixture was filtered and allowed to stand. The organic layer was isolated and dried over anhy. Na$_2$SO$_4$. The solvent was evaporated to obtain oily product. Yield was 10 g (64%).

EXAMPLE 24

(±)-Methyl (2-chlorophenyl)-(6,7-dihydro-4H-thieno[3,2-c]pyrid-5-yl)acetate hydrogen sulfate salt (I)

10 g of (+) Methyl (2-chlorophenyl)-(6,7-dihydro-4H-thieno[3,2-c]pyrid-5-yl)acetate prepared according to Example 22, was dissolved in 100 mL of ice-cold acetone and 2 mL concentrated sulfuric acid was added at 0° C. to 5° C. The crystalline white to off white product formed was isolated by filtration and washed with 20 mL of acetone. The product obtained was dried in vacuum oven at 50° C. The yield of titled product was 7.2 g (56%).

EXAMPLE 25

(±)-Methyl (2-chlorophenyl)-(6,7-dihydro-4H-thieno[3,2-c]pyrid-5-yl)acetate (I)

2 g (0.00652 mol) (±)-(2-chlorophenyl)-(6,7-dihydro-4H-thieno[3,2-c]pyrid-5-yl)acetamide and 2 mL (0.0308 mol) methane sulfonic acid and 20 mL methanol were mixed and the solution was refluxed at 85° C. for 12 hrs. The excess of solvent was removed under reduced pressure. The pH was adjusted to about 9 with aq. solution of sodium bicarbonate at 0° C., and the product was extracted with 70 mL ethyl acetate. The combined organic extracts were dried over anhy. Na$_2$SO$_4$ and concentrated. The residue obtained was purified by column chromatography using hexane:ethyl acetate as eluent. The product thus obtained was concentrated, was stored under nitrogen atmosphere, and kept in refrigerator before converting into salt. The yield of titled product was 0.419 g (20%).

EXAMPLE 26

(±)-Methyl (2-chlorophenyl)-(6,7-dihydro-4H-thieno[3,2-c]pyrid-5-yl)acetate (I)

1 g (0.00326 mol) (±)-(2-chlorophenyl)-(6,7-dihydro-4H-thieno[3,2-c]pyrid-5-yl)acetamide was dissolved in 20 mL methanol and refluxed at 85° C. During the reflux 10 mL polyphosphoric acid was added dropwise over a period of 1 hr and refluxing was continued for 6 hour. The excess of solvent was removed under reduced pressure. To the residue, 50 mL ethyl acetate was added at 0° C. and the reaction mixture was made basic with aq. NaHCO$_3$, up to pH 9. Out of the two phases separated, the organic layer was isolated, dried over anhydrous Na$_2$SO$_4$ and concentrated. The residue obtained was purified by column chromatography using hexane:ethyl acetate (9:1) as eluent. The product obtained was stored under nitrogen atmosphere and kept in refrigerator before converting into salt. The yield of titled product was 310 mg (30%).

EXAMPLE 27

(±)-Methyl (2-chlorophenyl)-(6,7-dihydro-4H-thieno[3,2-c]pyrid-5-yl)acetate (I)

1 g (0.00326 mol) (±)-(2-chlorophenyl)-(6,7-dihydro-4H-thieno[3,2-c]pyrid-5-yl)acetamide was added to 2 mL toluene at 0° C. along with stirring, followed by dropwise addition of 1 mL titanium tetrachloride, and the reaction was stirred at 0° C. for 1 hour. Later 18 mL of methanol was added, and then the reaction was stirred for 36 hour at 29° C. and later reflux for 3 hrs. The solvent was distilled under reduced pressure and the residue was added to aq. sodium carbonate at 0° C. the product was extracted with 20 mL ethyl acetate, and the organic layer was isolated, dried over anhy. Na$_2$SO$_4$, concentrated and purified by column chromatography using hexane:ethyl acetate as eluent. The product obtained was stored under nitrogen atmosphere and kept in refrigerator before converting into salt. The yield of titled product was 0.157 g (12–15%).

EXAMPLE 28

(±)-Methyl (2-chlorophenyl)-(6,7-dihydro-4H-thieno[3,2-c]pyrid-5-yl)acetate (I)

To 5 g (16.31 mmol) (±)-(2-chlorophenyl)-(6,7-dihydro-4H-thieno[3,2-c]pyrid-5-yl)acetamide, 25 mL POCl$_3$ was added under stirring. The contents were refluxed until amide was completely consumed (approx. 4 hr). Afterwards 20 mL methanol and 5 mL concentrated H$_2$SO$_4$ were added and stirred at room temperature for 1 hour. Later the reaction mixture was refluxed for 1 hour. The reaction mixture was quenched with aq. Na$_2$CO$_3$ at 0° C., and extracted with 200 mL ethyl acetate. The organic layer was isolated, dried over anhy. Na$_2$SO$_4$, concentrated and purified by column chromatography using hexane:ethyl acetate as eluent. The product obtained was stored under nitrogen atmosphere and kept in refrigerator before converting into salt. The yield of titled product was 0.943 g (18%).

EXAMPLE 29

(±)-Methyl(2-chlorophenyl)-(6,7-dihydro-4H-thieno[3,2-c]pyrid-5-yl)acetate (I)

1 g (0.00326 mol) (±)-(2-chlorophenyl)-(6,7-dihydro-4H-thieno[3,2-c]pyrid-5-yl)acetamide was dissolved in 10 mL methanol. The reaction mixture was saturated with HCl (g) at 0° C., was stirred at room temperature for 4 hrs, and later was refluxed for 6 hrs. The solvent was removed under reduced pressure. To the residue, 10 mL of ethyl acetate and aqueous NaHCO$_3$ until pH was 9 (at 0° C.) were added. The organic layer was isolated, dried over anhy. Na$_2$SO$_4$, evaporated under reduced pressure. The residue was further purified by column chromatography using hexane: ethyl acetate as eluent. The product obtained was stored under nitrogen atmosphere and kept in refrigerator before converting into salt. The yield of titled product was 0.188 g (18%).

EXAMPLE 30

(±)-Methyl(2-chlorophenyl)-(6,7-dihydro-4H-thieno[3,2-c]pyrid-5-yl)acetate (I)

To 1 g (0.00326 mol) (±)-(2-chlorophenyl)-(6,7-dihydro-4H-thieno[3,2-c]pyrid-5-yl)acetamide, 3 g (24.2 mmole) DMFDMA (dimethyl formamide dimethyl acetal) and 10 mL methanol were added. The reaction mixture was refluxed at 70° C. for 14 hr, and then poured in water and extracted with ethyl acetate. The combined organic layers are dried over anhy. Na$_2$SO$_4$, evaporated under reduced pressure. The residue was further purified by column chromatography using hexane:ethyl acetate (9:1) as eluent. The yield of titled product was 500 mg (48%).

EXAMPLE 31

(S)-(+)-(2-chlorophenyl)-(6,7-dihydro-4H-thieno[3,2-c]pyrid-5-yl)acetamide (II)

a) A solution of 5 g (16.31 mmol) of (±)-(2-chloro-phenyl)-(6,7-dihydro-4H-thieno[3,2-c]pyrid-5-yl)acetamide (prepared as given in Examples 10–15) and 4.15 g (16.2 mmol) (1S) (+)-camphor-10-sulphonic acid monohydrate in 100 mL acetone was stirred at room temperature for 20 h. Subsequently it was kept for 1 week in a freezer. Few crystals appeared concentration of volume by evaporating solvent under reduced pressure and repeated recrystallization in freezer for few days gave 3.3 g (75% yield) of (S)-2-(2-chloro-phenyl)-(4,5,6,7-tetrahydrothieno[3,2-c]pyrid-5-yl)acetamide (+)-camphor sulfonic acid salt. The salt was further purified by recrystallization in acetone, until constant specific optical rotation was obtained.

The product obtained was dried suitably. The typical physicochemical characteristics of the product obtained are as follows,

| | |
|---|---|
| Melting range | 223–225° C.(dec.) |
| SOR | +51°(C = 1, MeOH) | b) 3.3 g (S)-(+)-(2-chlorophenyl)-(6,7-dihydro-4H-thieno[3,2-c]pyrid-5-yl)acetamide 10-D-camphor sulfonic acid salt was added to 20 mL saturated aqueous Na$_2$CO$_3$ solution and the product was extracted with 20 mL ethyl acetate. The organic layer was isolated, dried over Na$_2$SO$_4$ and concentrated under reduced pressure. The product was obtained crude oil, which upon purification gives, 1.6 g of white crystals (64%).

The product obtained was characterized by different physico-chemical characteristics including IR spectrum, Mass, $^{13}$C-NMR and $^1$H-NMR, which are as given below;

| | |
|---|---|
| Melting point | 153–154° C. |
| SOR | +41°(C = 1, MeOH) |
| Optical purity | 99.5% by chiral HPLC column. |
| IR spectrum (cm$^{-1}$) | 1656(s, C = O group), 2333.7(m, C – N), 3357.9(s, N – H str). |
| Mass peaks (m/z) | 307.2(M + H)$^+$ |
| $^{13}$C-NMR (CDCl$_3$) | δ173.25, 134.84, 132.87, 132.65, 129.98, 129.56, 129.0, 126.72, 124.87, 122.64, 68.65, 50.43, 48.73, 25.28. |
| $^1$H-NMR (CDCl$_3$) | δ7.4–7.5(4H, m), 7.07(1H, d), 7.06(1H, d), 6.66(1H, d), 6.5(1H, s), 4.9(1H, s), 3.6(2H, q), 2.88(4H, m). |
| HPLC purity | 99.85% |

EXAMPLE 32

(S)-(+)-(2-chlorophenyl)-(6,7-dihydro-4H-thieno[3,2-c]pyrid-5-yl)acetamide (II)

a) 2 g (6.5 mmol) of (±)-(2-chloro-phenyl)-(6,7-dihydro-4H-thieno[3,2-c]pyrid-5-yl)acetamide was added to 30 mL acetone. 0.82 g (3.28 mmol) (1S)-(+)-camphor-10-sulfonic acid monohydrate in 10 mL acetone was added to above solution at 15–20° C. in 4 hrs. The reaction mixture was stirred for another 5 min, where a few crystals were formed. The solvent was distilled under reduced pressure and then the reaction mixture was kept in cold condition at temperature below 8° C. The precipitate formed was filtered and washed with solvent. The yield of titled product was 1.2 g (60%) with melting range=223–225° C. and [α]$_D$=+51° (C=1, CH$_3$OH).

b) To the suspension of 1.1 g of (+)-(S-(2-chlorophenyl)-(6,7-dihydro-4H-thieno[3,2-c]pyrid-5-yl)acetamide (1S-(+)-camphor-10-sulfonic acid salt in 50 mL water, 50 mL of saturated Na$_2$CO$_3$ solution in water was added. The reaction mixture was stirred for some time, and was followed by addition of 100 mL ethyl acetate. The organic layer was isolated, and distilled to get the title product. The amount of product obtained was 600 mg (60%, based upon the dextroisomer present in the racemic mixture).

The product obtained was characterized by different physico-chemical characteristics, which are as given below;

| Melting range | 149–153° C. |
|---|---|
| [α]$_D$ | +38°(C = 1, CH$_3$OH) with % ee = 97.24%. |

EXAMPLE 33

(S)-(+)-(2-chloro-phenyl)-(6,7-dihydro-4H-thieno[3,2-c]pyrid-5-yl)acetamide (II)

a) 5 g (16.3 mmol) (±)-(2-chlorophenyl)-(6,7-dihydro-4H-thieno[3,2-c]pyrid-5-yl)acetamide was added to 60 mL ethyl acetate. 2 g (8.6 mmol) of (1S)-(+)-camphor-10-sulfonic acid monohydrate was dissolved in minimum amount of water and added to the above solution in one lot, and stirred at 35–40° C. for 1 hr. In short time salt forms and was isolated, washed with 50 mL acetone and dried. The amount of product obtained was 1.81 g (36%).

The product obtained was characterized by different physico-chemical characteristics, which are as given below,

| Melting range | 223–225° C. |
|---|---|
| [α]$_D$ | +52.12°(C = 1, CH$_3$OH). | b) To the suspension of 1.8 g of (S)-(+)-(2-chloro-phenyl)-(6,7-dihydro-4H-thieno[3,2-c]pyrid-5-yl) acetamide (1S)-(+)-camphor-10-sulfonic acid salt in 100 mL water, 50 mL of sodium bicarbonate solution in water was added. After stirring the mixture, 150 mL ethyl acetate was added. The combined organic layers are distilled off to get title product. The amount of product obtained was 1 g (56%).

The product obtained was characterized by different physico-chemical characteristics, which are as given below, similar to example 31;

| Melting range | 153–154° C. |
|---|---|
| [α]$_D$ | +42°(C = 1, CH$_3$OH) and with % ee = 100% (by chiral HPLC column chromatography). |

EXAMPLE 34

(R)-(−)-(2-chloro-phenyl)-(6,7-dihydro-4H-thieno[3,2-c]pyrid-5-yl)acetamide (II)

a) 5 g (+)-(2-chlorophenyl)-(6,7-dihydro-4H-thieno[3,2-c]pyrid-5-yl)acetamide (I) (0.016 mol) was added to 60 mL ethyl acetate and to the solution 2 g (0.0086 mol) (1R)-(−)-camphor-10-sulfonic acid monohydrate in 5 mL water was added to it in one lot. Reaction mixture was stirred at ambient temperature for 1 hr. Later the reaction mixture was stored in freezer for 1 week, a few crystals were seen. After, evaporation of solvent at reduced pressure and storing in cold condition the salt precipitated out, which was then filtered and washed with 50 mL acetone. The amount of product obtained was 1.7 g (39%).
The product obtained was characterized by different physico-chemical characteristics of (R)-(−)-(2-chlorophenyl)-(6,7-dihydro-4H-thieno[3,2-c]pyrid-5-yl)acetamide and of its (−)-CSA salt, both which are as given below;

| Melting range (−)-CSA-(−)acetamide | 219–220° C. |
|---|---|
| [α]$_D$ (−)-CSA-(−)acetamide | −52.12°(C=1, CH$_3$OH) | b) To the suspension of 1.6 g (R)-(−)-(2-chloro-phenyl)-(6,7-dihydro-4H-thieno[3,2-c]pyrid-5-yl)acetamide (1R)-(−)-camphor-10-sulfonic acid salt in 100 mL water, 50 mL of sodium bicarbonate solution in water was added. After stirring the mixture, 150 mL ethyl acetate was added. The organic layer was extracted and combined organic layer was distilled off to get title product. The amount of product obtained was 900 mg (36%).

The product obtained was characterized by different physico-chemical characteristics, which are as given below;

| Melting range | 145–149° C. |
|---|---|
| [α]$_D$acetamide | −36.49° (C = 1, CH$_3$OH) |

EXAMPLE 35

(S)-(+)-Methyl (2-chlorophenyl)-(6,7-dihydro-4H-thieno[3,2-c]pyrid-5-yl)acetate Bisulfate (I)

15 g of (+) (S)-(2-chloro-phenyl)-(6,7-dihydro-4H-thieno[3,2-c]pyrid-5-yl)acetamide (0.0489 mol), was converted into corresponding ester as given in example 23. The ester can be converted into its hydrogen sulfate salt, according to the procedure given in example 24. The amount of product obtained was 7 g (44.5%), with melting point=184–185° C.

The melting point, IR spectrum and XRD of the product obtained resembles that of product obtained in EP 281459 and U.S. Pat. No. 4,847,265 i.e. now referred as form I polymorph of Clopidogrel bisulfate (WO 99/65915).

The product obtained was characterized by different physico-chemical characteristics, as given below;

| [α]$_D$ | +55° (C = 1, CH$_3$OH) |
|---|---|
| Melting point | 185° C. ± 2° C. |
| IR spectrum | 2980, 1755, 1224, 1175 and 840 respectively with the respective % of percentage ransmittance of approximately: 45; 16; 19; 15; 45. |

XRD was found matching with the form I, XRD reported in WO 99/65915.

EXAMPLE 36

(R)-(−)-Methyl (2-chlorophenyl)-(6,7-dihydro-4H-thieno[3,2-c]pyrid-5-yl)acetate Bisulfate (I)

Using 5 g (R)-(−)-(2-chloro-phenyl)-(6,7-dihydro-4H-thieno[3,2-c]pyrid-5-yl)acetamide obtained in the above example 34, can be converted into ester as given in Example 23. Later the ester can be converted into hydrogen sulfate salt as given in Example 24. The amount of product obtained was 3.01 g (44%).

The product obtained was characterized by different physico-chemical/purity characteristics, as given below;

| | |
|---|---|
| [α]$_D$ | −52° (C = 1, CH$_3$OH) |

EXAMPLE 37

(S)-(+)-Methyl (2-chlorophenyl)-(6,7-dihydro-4H-thieno[3,2-c]pyrid-5-yl) acetate Bisulfate (I)

a) 10 g (0.0185 mol) (1S)-(+)-camphor-10-sulfonic acid salt of (+)-(2-chlorophenyl)-(6,7-dihydro-4H-thieno[3,2-c]pyrid-5-yl)acetamide was dissolved in 40 ml methanol at 0° C. To the solution 15 mL (0.28 mol) of conc. H$_2$SO$_4$ was added dropwise within 1.5 hr. Gradually the reaction temperature was increased, and it was refluxed for 26 hrs. In the end, the solvent was distilled off under reduced pressure. The residue left behind was mixed with 120 mL of ethyl acetate and the pH was adjusted between 9 to 10 using aq. sodium carbonate for extraction. The organic layer was isolated, dried over anhydrous Na$_2$SO$_4$, and evaporated under vacuum. The product obtained was purified by column chromatography using hexane: ethyl acetate (9:1) as eluent. The combined eluent was evaporated at reduced pressure to yield 5.76 g (97%) of product.

b) 2 g (S)-(+)-Methyl (2-chlorophenyl)-(6,7-dihydro-4H-thieno[3,2-c]pyrid-5-yl)acetate was converted into bisulfate salt according to the procedure given in Example 24. The product obtained was 2.2 g (84%) of product and found identical to that obtained in example 35.

EXAMPLE 38

Polymorph I of (+)-Methyl (2-chlorophenyl)-(6,7-dihydro-4H-thieno[3,2-c]pyrid-5-yl) acetate Bisulfate Salt (I)

52.5 mL of ice-cold acetone was added to 17.5 g (+)-Methyl (2-chlorophenyl)-(6,7-dihydro-4H-thieno[3,2-c]pyrid-5-yl)acetate while stirring at 0° C. 3.6 mL of concentrated H$_2$SO$_4$ was added dropwise and temperature was kept below 5° C. 20 mL of acetone was further added and reaction mixture was further stirred for 4 hrs at room temperature. Precipitate was isolated (17 g, 74%), dried under vacuum at temperature not exceeding 50° C.

The product obtained was characterized by different physico-chemical characteristics and was found identical to that obtained in example 35, as given below;

| | |
|---|---|
| Specific optical rotation | +54° (C = 1, CH$_3$OH) |
| Melting point | 185° C. ± 2° C. |

IR and XRD were found matching to that reported in the literature.

EXAMPLE 39

Polymorph I of (+)-Methyl (2-chlorophenyl)-(6,7-dihydro-4H-thieno[3,2-c]pyrid-5-yl)acetate Bisulfate Salt (I)

2.1 g (+)-Methyl (2-chlorophenyl)-(6,7-dihydro-4H-thieno[3,2-c]pyrid-5-yl)acetate was added 7.6 mL of acetone to obtain a clear solution. To this solution, 0.887 g of H$_2$SO$_4$ (80%) was added slowly and temperature was maintained around 20° C. under nitrogen atmosphere. Later the reaction mixture was cooled upto −20° C. for 2 hrs and then the temperature was brought to room temperature (20° C.). The reaction mixture was stirred at 20–25° C. Precipitate was isolated (600 mg), dried under vacuum at temperature not exceeding 50° C.

The product obtained was characterized by different physico-chemical characteristics and was found identical to that obtained in example 35, as given below;

| | |
|---|---|
| SOR (α$^D$) | +54.03° (C = 1.89, MeOH) |
| Melting point | 185° C. ± 1° C. |
| Chiral Purity | 99.63% (ee) |

IR and XRD were found matching to that reported in the literature.

EXAMPLE 40

Polymorph I of (+)-Methyl (2-chlorophenyl)-(6,7-dihydro-4H-thieno[3,2-c]pyrid-5-yl)acetate Bisulfate Salt (1)

To 2 g (+)Methyl (2-chlorophenyl)-(6,7-dihydro-4H-thieno[3,2-c]pyrid-5-yl)acetate was added 5 mL of acetone and stirred at 25–30° C. The temperature of the reaction mixture was raised from 25 to 65° C. and then kept at 65° C. for 5 min. At temperature 50–52° C. 0.676 g of concentrated H$_2$SO$_4$ was added. The reaction mixture was cooled from 52° C. to 5° C., and additional acetone was added and stirred for 5 min. Later the reaction mixture was stirred at 25–30° C. for 12 hrs, the thick precipitate obtained was filtered, washed with 5 mL of acetone and the residue was dried in a vacuum oven. The yield of titled product obtained was 1.27 g (47%).

The product obtained was characterized by different physico-chemical characteristics and was found identical to that obtained in example 35, as given below;

| | |
|---|---|
| SOR(α$^D$) | +54.03° (C = 1.89, MeOH) |
| Melting point | 185° C. ± 1° C. |
| Chiral Purity | 99.80% (ee) |

IR and XRD were found matching to that reported in the literature.

EXAMPLE 41

Polymorph I of (+)-Methyl (2-chlorophenyl)-(6,7-dihydro-4H-thieno[3,2-c]pyrid-5-yl)acetate Bisulfate Salt (I)

To 1.98 g (+)-Methyl (2-chlorophenyl)-(6,7-dihydro-4H-thieno[3,2-c]pyrid-5-yl)acetate was added 5 mL of acetone and stirred at 25–30° C. The temperature of the reaction mixture was raised from 25 to 50–52° C. and within one lot 0.7 g of concentrated H$_2$SO$_4$ (95%) was added with constant stirring and the reaction mixture was suddenly cooled to 0° C. to −5° C. for 10 min. Later the reaction mixture was stirred at 25–30° C. for 12 hrs, the thick precipitate obtained was filtered, washed with 5 mL of acetone and the residue (1.6 g, 62%) was dried in a vacuum oven.

The product obtained was characterized by different physico-chemical characteristics and was found identical to that obtained in example 35, as given below,

| | |
|---|---|
| SOR ($\alpha^D$) | +55.96° (C = 1.89, MeOH) |
| Melting point | 185° C. ± 1° C. |
| Chiral Purity | 99.85% (ee) |

IR and XRD were found matching to that reported in the literature.

EXAMPLE 42

Racemization of (R)-(−)-(2-chlorophenyl)-(6,7-dihydro-4H-thieno[3,2-c]pyrid-5-yl)acetamide (II)

20 g mixture of laevorotatory (R)-(−)-(2-chlorophenyl)-(6,7-dihydro-4H-thieno[3,2-c]pyrid-5-yl)acetamide of formula (II) and 11 g of potassium t-butoxide in 100 mL of t-butanol was stirred at 25° C. to 30° C. for 30 min. After completion of reaction, the reaction mixture was poured in 750 mL cold water to obtain a yellow precipitate. This solid obtained was filtered and dissolved in methylene dichloride. The organic layer was washed with 2×100 mL of DM water (2×100 mL) and concentrated to give 18 g of the corresponding racemic amide i.e. (±)2-(2-chlorophenyl)-(6,7-dihydro-4H-thieno[3,2-c]pyrid-5-yl)acetamide (II).

The specific optical rotation of racemic amide (II) was ±1° (C=1, $CH_3OH$).

EXAMPLE 43

Racemization of (R)-(−)-(2-chlorophenyl)-(6,7-dihydro-4H-thieno[3,2-c]pyrid-5-yl)acetamide (II)

1 g mixture of laevorotatory (R)-(−)-(2-chlorophenyl)-(6,7-dihydro-4H-thieno[3,2-c]pyrid-5-yl)acetamide of formula (II) and 1 g of potassium t-butoxide in 20 mL of DMSO was stirred at 50° C. to 60° C. for 3 hours. After completion of reaction, the reaction mixture was poured in 150 mL cold water to obtain a yellow precipitate. This solid obtained was filtered and dissolved in methylene dichloride. The organic layer was washed with 2×25 mL of DM water (2×25 mL) and concentrated to give 0.8 g of the corresponding racemic amide i.e. (±)-2-(2-chlorophenyl)-(6,7-dihydro-4H-thieno[3,2-c]pyrid-5-yl)acetamide.

The specific optical rotation of racemic amide (II) was ±0.50 (C=1, $CH_3OH$).

EXAMPLE 44

Racemization of (R)-(−)-(2-chlorophenyl)-(6,7-dihydro-4H-thieno[3,2-c]pyrid-5-yl)acetamide (II)

1 g mixture of laevorotatory (R)-(−)-(2-chlorophenyl)-(6,7-dihydro-4H-thieno[3,2-c]pyrid-5-yl)acetamide of formula (II) and 250 mg of sodium hydride in dry tetrahydrofuran was stirred at 25° C. to 30° C. for 3 hours. After completion of reaction, the reaction mixture was poured in 150 mL cold water slowly to obtain a yellow precipitate. This solid obtained was filtered and dissolved in methylene dichloride. The organic layer was washed with 2×25 mL of DM water (2×25 mL) and concentrated to give 0.95 g of the corresponding racemic amide i.e. (±)-(2-chlorophenyl)-(6,7-dihydro-4H-thieno[3,2-c]pyrid-5-yl)acetamide (II).

EXAMPLE 45

Racemization of (R)-(−)-(2-chlorophenyl)-(6,7-dihydro-4H-thieno[3,2-c]pyrid-5-yl)acetamide (II)

1 g mixture of laevorotatory (R)-(−)-(2-chlorophenyl)-(6,7-dihydro-4H-thieno[3,2-c]pyrid-5-yl)acetamide of formula (II) and 21 g of potassium t-butoxide in 100 mL of DMSO was stirred at 50° C. to 60° C. for 3 hours. After completion of reaction, the reaction mixture was poured in 750 ml cold water to obtain a yellow precipitate. This solid obtained was filtered and dissolved in methylene dichloride. The organic layer was washed with 2×100 mL of DM water (2×100 mL) and concentrated to give 0.8 g of the corresponding racemic amide i.e. (±)-(2-chlorophenyl)-(6,7-dihydro-4H-thieno[3,2-c]pyrid-5-yl)acetamide.

EXAMPLE 46

(S)-(+)-Methyl (2-chlorophenyl)-(6,7-dihydro-4H-thieno[3,2-c]pyrid-5-yl)acetate (I)

5 g of (+)-(2-chlorophenyl)-(6,7-dihydro-4H-thieno[3,2-c]pyrid-5-yl)acetamide was dissolved in 35 ml methanol and the solution was chilled to 0 to −5° C. 15 mL (0.28 mole) of conc. $H_2SO_4$ (98%) was added slowly in 1 hr maintaining the temperature till −5° C. After the completion of addition the reaction mixture was stirred at room temperature for 30 min. The solution was refluxed at 60° C. for 36 hrs. The reaction mixture was cooled to room temperature and the solvent was distilled off under reduced pressure. The residue was added to 200 mL chilled water was added and cooled to −5° C. The pH of reaction mixture was adjusted between 9 to 10 using aq. sodium carbonate. The residue was extracted with 100 mL ethyl acetate. The organic layer was dried over anhydrous $Na_2SO_4$, and evaporated under vacuum. The combined eluent was evaporated at reduced pressure to yield 3.2 g of purified product purified by column chromatography, using hexane: ethyl acetate (9:1) as eluent.

EXAMPLE 47

(S)-(+)-Methyl (2-chlorophenyl)-(6,7-dihydro-4H-thieno[3,2-c]pyrid-5-yl)acetate (I)

5 g of (+)-(2-chlorophenyl)-(6,7-dihydro-4H-thieno[3,2-c]pyrid-5-yl)acetamide was dissolved in 45 ml methanol, followed by 15 mL of toluene. 5 mL (0.28 mol) of conc. $H_2SO_4$ was instantly added and another 10 mL of conc. $H_2SO_4$ was slowly added later, while maintaining the temperature at 90° C. After that, the reaction mixture was refluxed at 90° C. for 13 hrs. The solvent was distilled off under reduced pressure. To the residue, 50 mL of water was added and the pH of reaction mixture was adjusted between 9 to 10 using aq. sodium carbonate. The residue was extracted with 100 mL ethyl acetate. The organic layer was dried over anhydrous $Na_2SO_4$, and evaporated under vacuum. The combined eluent was evaporated at reduced pressure to yield 2.8 g of crude product purified by column chromatography, using hexane:ethyl acetate (9:1) as eluent.

EXAMPLE 48

(S)-(+)-Methyl (2-chlorophenyl)-(6,7-dihydro-4H-thieno[3,2-c]pyrid-5-yl)acetate (I)

5 g of (S)-(+)-(2-chlorophenyl)-(6,7-dihydro-4H-thieno[3,2-c]pyrid-5-yl)acetamide was dissolved in 50 ml methanol and the solution was cooled till −15° C. 15 mL (0.28 mol) of conc. $H_2SO_4$ (98%) was added dropwise in 1 hr maintaining the temperature till −15° C. After the completion of addition the reaction mixture was gradually increased, and stirred at 31° C. for 30 min, and then refluxed at 70° C. for 21 hrs. The solvent was distilled off under reduced pressure and to the residue 50 mL of water was added and stirred for 30 min followed by cooling to −5° C.

The pH of reaction mixture was adjusted between 9 to 10 using aq. sodium carbonate. The residue was extracted with 100 mL ethyl acetate. The organic layer was dried over anhydrous $Na_2SO_4$, and evaporated under vacuum. The yield was 3.8 g of crude product purified by column, using hexane:ethyl acetate (9:1) as eluent.

EXAMPLE 49

(S)-(+)-Methyl (2-chlorophenyl)-(6,7-dihydro-4H-thieno[3,2-c]pyrid-5-yl)acetate (I)

5 g of (+)-(2-chlorophenyl)-(6,7-dihydro-4H-thieno[3,2-c]pyrid-5-yl)acetamide was dissolved in 20 ml methanol and the solution warmed to 65 to 70° C. 15 mL (0.28 mol) of chilled conc. $H_2SO_4$ (98%, −15° C.) was added slowly in 1 hr maintaining the temperature till −15° C. After the completion of addition the reaction mixture was heated at 70° C. for 16 hrs. The solvent was distilled off under reduced pressure and to the residue 50 mL of water was added and stirred for 30 min followed by cooling to −5° C. The pH of reaction mixture was adjusted between 9 to 10 using aq. sodium carbonate. The residue was extracted with 100 mL ethyl acetate. The organic layer was dried over anhydrous $Na_2SO_4$, and evaporated under vacuum. The combined eluent was evaporated at reduced pressure to yield 2.8 g of crude product purified by column chromatography, using hexane:ethyl acetate (9:1) as eluent to give 2 g of titled compound (1) and 1 g of the starting material (S)-(+)-(II).

EXAMPLE 50

(S)-(+)-(2-chlorophenyl)-(6,7-dihydro-4H-thieno[3,2-c]pyrid-5-yl)acetamide (II)

a) A solution of 5 g (16.31 mmol) of (±)-(2-chloro-phenyl)-(6,7-dihydro-4H-thieno[3,2-c]pyrid-5-yl) acetamide (prepared as given in Examples 10–15) and 4.15 g (16.2 mmol) (1S)-(+)-camphor-10-sulphonic acid monohydrate in 100 mL acetone was kept warm for 20 hrs followed by storing it in temperature below 10° C. A few crystals appeared, the mother liquor was concentrated further and repeated recrystallization, followed by storage in cold condition for few days gave 3.1 g (70% yield) of (S)-2-(2-chloro-phenyl)-(4,5,6,7-tetrahydrothieno[3,2-c]pyrid-5-yl) acetamide (+)-camphor sulfonic acid salt. The salt was further purified by recrystallization in acetone, until constant specific optical rotation was obtained.

The product obtained was dried suitably. The typical physicochemical characteristics of the product obtained are as follows,

| Melting range | 223–225° C. (dec.) |
| SOR | +52° (C = 1, MeOH) | b) 3.1 g (S)-(+)-(2-chlorophenyl)-(6,7-dihydro-4H-thieno[3,2-c]pyrid-5-yl)acetamide 10-D-camphor sulfonic acid salt was added to 20 mL saturated $Na_2CO_3$ solution and the product was extracted with 20 mL ethyl acetate. The organic layer was isolated, dried over $Na_2SO_4$ and concentrated under reduced pressure. The product was obtained crude oil, which upon purification gives, 1.5 g of white crystals (60%).

EXAMPLE 51

Chiral Removal of (−)-Stereoisomer from a Mixture Containing Excess of (+)-Methyl (2-chlorophenyl)-(6,7-dihydro-4H-thieno[3,2-c]pyrid-5-yl)acetate (I)

2 g (0.0173 mole) Methyl (2-chlorophenyl)-(6,7-dihydro-4H-thieno[3,2-c]pyrid-5-yl)acetate (where ee was 80%) was dissolved in 10 ml acetone and the reaction mixture was stirred for 10 min, followed by reflux. To the reaction mixture, 1.49 g (1S)-(+)-camphor-10-sulfonic acid hydrate in 0.8 mL water was added followed by 1 mL acetone. Then whole reaction mixture was refluxed for 1 hrs and cooled gradually. This was later stirred overnight at room temperature. The clear solution was cooled further at 0 to −5° C., wherein precipitate was obtained. The salt formed was added to ethyl acetate and water, which was later basified with $NaHCO_3$, the organic layer was washed with water, concentrated under reduced pressure, to give free base 0.386 g with chiral purity=99.85% (+)-isomer (ee=99.7%).

EXAMPLE 52

Chiral Removal of (−)-Stereoisomer from a Mixture Containing Excess of (+)-Methyl (2-chlorophenyl)-(6,7-dihydro-4H-thieno[3,2-c]pyrid-5-yl)acetate (I)

2 g (0.0173 mole) Methyl (2-chlorophenyl)-(6,7-dihydro-4H-thieno[3,2-c]pyrid-5-yl)acetate (where ee was 90%) was dissolved in 10 ml acetone and the reaction mixture was stirred for 10 min, followed by reflux. To the reaction mixture, 1.49 g (1S)-(+)-camphor-10-sulfonic acid hydrate in 0.8 mL water was added followed by 1 mL acetone. Then whole reaction mixture was refluxed for 1 hrs and cooled gradually. This was later stirred overnight at room temperature. The clear solution was cooled further at 0 to −5° C., wherein precipitate was obtained. The salt formed was added to ethyl acetate and water, which was later basified with $NaHCO_3$, the organic layer was washed with water, concentrated under reduced pressure, to give free base 0.386 g with chiral purity=99.85% (+)-isomer (ee=99.7%).

EXAMPLE 53

Chiral Removal of (−)-Stereoisomer from a Mixture Containing Excess of (+)-Methyl (2-chlorophenyl)-(6,7-dihydro-4H thieno[3,2-c]pyrid-5-yl)acetate (I)

2 g (0.0173 mole) Methyl (2-chlorophenyl(6,7-dihydro-4H-thieno[3,2-c]pyrid-5-yl)acetate (where ee was 95%) was dissolved in 10 ml acetone and the reaction mixture was stirred for 10 min, followed by reflux. To the reaction mixture, 1.49 g (1S)-(+)-camphor-10-sulfonic acid hydrate in 0.8 mL water was added followed by 1 mL acetone. Then whole reaction mixture was refluxed for 1 hrs and cooled gradually. This was later stirred overnight at room temperature. The clear solution was cooled further at 0 to −5° C., wherein precipitate was obtained. The salt formed was added to ethyl acetate and water, which was later basified with $NaHCO_3$, the organic layer was washed with water, concentrated under reduced pressure, to give free base 0.386 g with chiral purity=99.85% (+)-isomer (ee=99.7%).

EXAMPLE 54

Resolution of (±)-Methyl (2-chlorophenyl)-(6,7-dihydro-4H-thieno[3,2-c]pyrid-5-yl)acetate (I)

33 g (0.1 mol) (±)-Methyl (2-chlorophenyl)-(6,7-dihydro-4H-thieno[3,2-c]pyrid-5-yl)acetate was dissolved in 200 ml acetone and the reaction mixture was heated to 60 to 70° C., reflux for 15 min. To the reaction mixture, 25.6 g (1S)-(+)-camphor-10-sulfonic acid hydrate dissolved in water was added, wherein formation of salt starts at 60 to 70° C. After the formation of salt was complete, the reaction mixture was cooled gradually to room temperature and then to 0° C. to 5° C. The isolation of diastereomeric salt by filtration and washed using acetone, and dried. The yield of the diastereomeric product was 20.5 g (70%).

Generation of (−) isomer of title compound was carried out using dilute sodium bicarbonate solution and extraction in ethyl acetate, removal of solvent to give the title compound 10.9 g (66%).

EXAMPLE 55

Resolution of (±)-(2-chlorophenyl)-(6,7-dihydro-4H-thieno[3,2-c]pyrid-5-yl)acetonitrile (IV)

a) To 5 g (0.0173 mol) (±)-(2-chlorophenyl)-(6,7-dihydro-4H-thieno[3,2-c]pyrid-5-yl)acetonitrile dissolved in 100 ml acetone, 4.35 g (0.0174 mole) (1S)-(+)-camphor-10-sulfonic acid hydrate in 5 mL water was added in one lot at 60 to 62° C. during addition. The mixture is stirred at 60° C. for 60 hr. the stirring was then continued overnight and later kept in refrigerator for 1 day. The diastereomeric salt precipitated was then filtered to yield 730 mg of product.

b) To 730 mg (±)-(2-chlorophenyl)-(6,7-dihydro-4H-thieno[3,2-c]pyrid-5-yl)acetonitrile (1S)-(+)-camphor-10-sulfonic acid salt in 20 mL water, 10 mL (5%) Na$_2$CO$_3$ solution added (pH=10). After stirring the mixture, 100 mL ethyl acetate was added to it organic layer was then added to it. Organic layer was then separated and distilled off to get product. The yield of product was 400 mg (16%).

Specific optical rotation($\alpha^D$): +7.5787° (C=1, DMF).

We claim:

1. A process for the preparation of compound of formula (I),

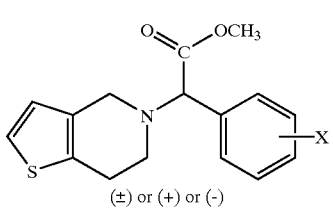

(±) or (+) or (−)

where X represents either hydrogen, fluoro, chloro, bromo or iodo atom which comprises:

i) reacting a compound of formula (V) or its salt,

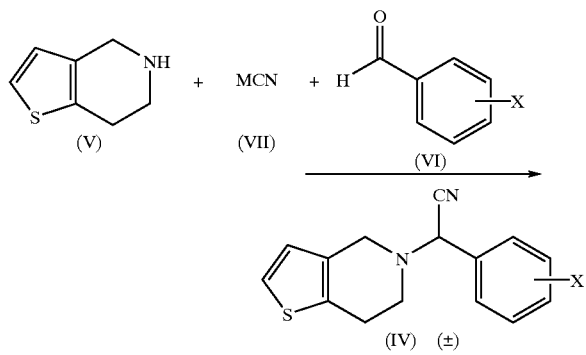

with a cyanide of general formula (VII) where M represents alkali metal, trimethysilyl, Cu, or hydrogen, followed by addition of compound of general formula (VI), where X is as defined earlier, to obtain a racemic compound of general formula (IV), where X is as defined earlier;

ii) reacting a compound of general formula (IV), in (±) form or any of its optically active (+), or (−) forms,

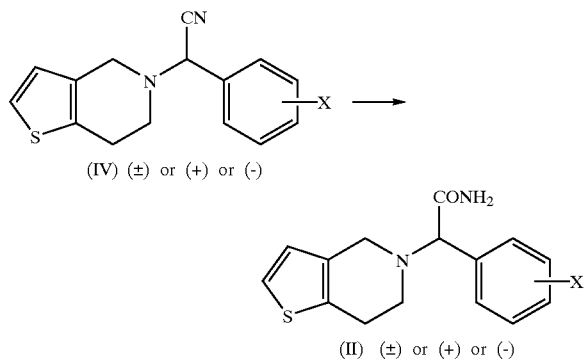

with acidic or basic reagents to obtain a compound of formula (II) or its salt with retention of configuration;

iii) reacting a compound of general formula (II), in either (±) form or its optically active (+) or (−) forms;

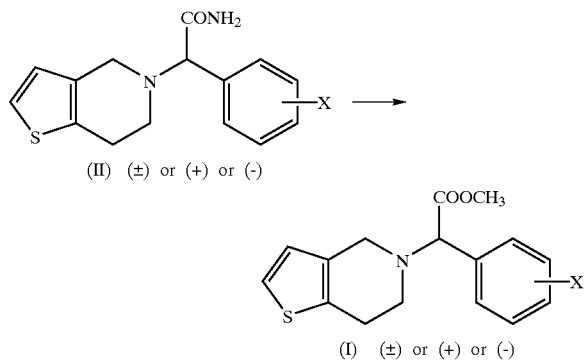

with acidic reagents in presence of methanol to obtain a compound of formula (I) or its salt, with retention of configuration; and iv) resolving the (±) form of the compound of formula (I) or its salt if formed into its optical isomers.

2. A process according to claim 1, wherein optionally, there is included the step of resolving a racemic compound of formula (IV) into its optical isomers, or else, transforming the racemic compound or its optical isomers into its salts, followed by liberation of the salt from the compound.

3. A process according to claim 1, wherein optionally, there is included the step of resolving a racemic compound of formula (II) into its optical isomers, or else, transforming the racemic compound or its optical isomers into its salts, followed by liberation of the salt from the compound.

4. A process for the preparation of compound of formula (III) or its salt, where X represents hydrogen, chloro, bromo or iodo atom which comprises:

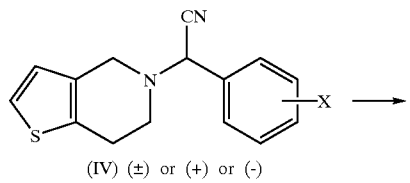

(IV) (±) or (+) or (−)

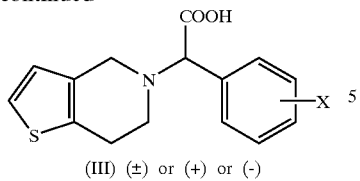

(III) (±) or (+) or (-)

i) reacting a compound of general formula (IV) or salt thereof, in any of its optical forms, in presence of acidic/basic catalyst in a suitable solvent, giving the corresponding acid of formula (III) or its salt, with a configuration that is the same as that of the starting material; and ii) optionally resolving any racemic compound of formula (III) or its salt, into its corresponding optically pure (+) and (−) forms.

5. A process according to claim 1, wherein (2-chlorophenyl)-(6,7-dihydro-4H-thieno[3,2-c]pyrid-5-yl) acetamide, a compound of formula (II), or its optical active isomers or its salts, where X represents a halogen atom such as chloro, bromo, iodo substituent is prepared by a process comprising:

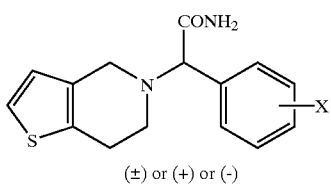

(±) or (+) or (-)

i) treating the compound of formula (IV) or its salt or any of its optical forms, with basic reagents when the starting material is racemic, or with an acidic catalyst when the starting material is optically active, in the presence of a suitable solvent to form a salt of a compound of formula (II); and ii) resolving the product of step (i) into its corresponding optically pure (+) and (−) forms.

6. A process according to claim 5, which comprises preparation of said compound of formula (II) characterized in that the basic reagent used is selected from the group consisting of: lithium hydroxide, potassium hydroxide, sodium hydroxide and potassium t-butoxide.

7. A process according to claim 5, which comprises preparation of said compound of formula (II), wherein said acidic reagent used is selected from the group consisting of: acetic acid, p-toluenesulfonic acid, trifluoroacetic acid, chloroacetic acid, perchloric acid, formic acid or mineral acids, or aqueous hydrochloric acid, sulfuric acid, HBr or a mixture thereof.

8. A process according to claim 5, which comprises preparation of said compound of formula (II) wherein, the solvent used is selected from the group consisting of: water, $C_1$–$C_4$) alcohol, acetone, acetic acid, dimethylformamide, THF, DMSO, dioxane, DME and the like or mixtures thereof, preferably, mixture of water, methanol or tert-BuOH.

9. A process according to claim 5, wherein a racemic mixture of said compound of formula II, is resolved into (−) and its (+) forms using 1-(R) or 1 (S)-camphorsulfonic-10-acid, or tartaric acid, in the presence of solvent.

10. A process according to claim 5, a racemic mixture of said compound of formula II, is converted into a salt, using a compound selected from the group consisting of: D-camphorsulfonate, L-camphor sulfonate, D-tartaric acid, L-tartaric acid or hydrogen sulfate.

11. A process according to claim 1, wherein said compound of formula (I) is Methyl (2-chlorophenyl)-(6,7-dihydro-4H-thieno[3,2-c]pyrid-5-yl)acetate, or its optical active isomers or its salts, where X represents a halogen atom such as chloro, bromo, iodo substituent, and said process comprises the steps of:

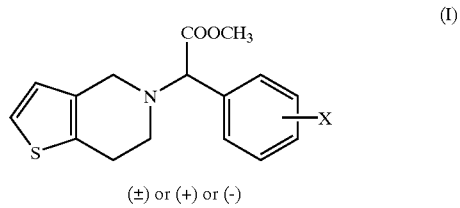

(±) or (+) or (-)

i) treating the compound of formula (II), or its salt, or, any of its optical forms, with acidic reagents, in the presence of suitable solvent to form a salt of the compound of formula (I); and ii) resolving the product of step (i) into its corresponding optically pure (+) and (−) forms.

12. A process according to claim 11, wherein said acidic reagent used is concentrated sulfuric acid in the range from 1 equivalent to 50 equivalents.

13. A process according to claim 11, wherein, the solvent used is methanol in the range of 3 to 30 volumes, along with other cosolvents.

14. A process according to claim 11, wherein the duration of step (i) ranges from 4 hrs to 4 days.

15. A process defined in claim 11, wherein step (i) is carried out at a temperature in range from 40° C. to 140° C.

16. A process according to claim 11, wherein said salt of compound of formula (I) is resolved using a resolving agent selected from the group consisting of: 1-(R) or 1-(S)-camphorsulfonic-10-acid, (R) or (S)-tartaric acid, and 1-(R) or 1-(S) camphorsulfonic-10-acid, and wherein the resolving agent is in the presence of a solvent.

17. A process according to claim 16, wherein the salt of formula I is a mixture containing varying ratios of the two enantiomers (−)-I and (+)-I, and such salt is resolved to the (+)-(I)-stereoisomer by chiral enrichment, or by chiral removal of the (−)-(I) enantiomer.

18. A process for the preparation of a compound of formula (IV) and its salts,

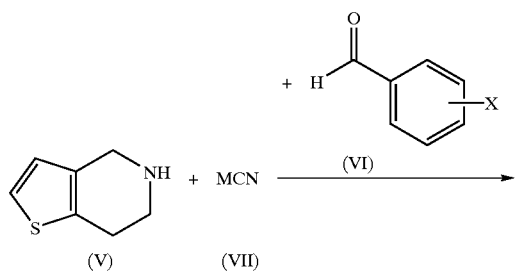

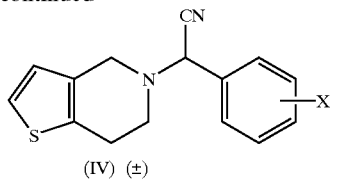

(IV) (±)

where X represents a halogen atom such as chloro, bromo, iodo substituent which comprises:
  i) reacting a compound of general formula (V) or its acid addition salt with a cyanide of general formula (VII), wherein M is selected from the group consisting of: alkali metal, TMS, Cu, and hydrogen, followed by reaction with a halogenobenzaldehyde of the formula (VI), wherein X is halogen atom; or
  ii) reacting a halogenobenzaldehyde of general formula (VI), wherein the meaning of X is halogen atom, with cyanide of general formula (VII), wherein M is selected from the group consisting of: alkali metal, TMS, Cu, and hydrogen, followed by in situ reaction with the compound of general formula (V) or its acid addition salt; or,
  iii) reacting a halogenobenzaldehyde of general formula (VI) wherein the meaning of X is halogen atom, with hydrogen sulfite of general formula (VIII),

M'HSO₃  (VIII)

wherein M is selected from the group consisting of: alkali metal, TMS, Cu, and hydrogen, and then with cyanide of general formula (VII), wherein M is selected from the group consisting of: alkali metal, TMS, Cu, and hydrogen, and subsequently reacting in situ with the compound of general formula (V) or its acid addition salt followed by resolving of the compound of formula (IV) or its salt, so as to obtain to its optically pure (+) and (−) form.

19. The process according to claim 18 wherein the reaction is carried out at temperature between about −30° C. and about 100° C.

20. The process according to claim 18 wherein the process is carried out in an aqueous or a non-aqueous medium containing acids.

21. The process according to claim 18 wherein a catalyst acid selected from the group consisting of: dry hydrochloric acid, sulfuric acid, p-toluenesulfonic acid and acetic acid, is used.

22. A process according to claim 18 wherein a compound of formula (IV), (±)-(2-chlorophenyl) (6,7-dihydro-4H-thieno[3,2-c]pyrid-5-yl)acetonitrile, is resolved into its (−) and (+) forms using a resolving agent selected from the group consisting of: 1(R) or 1(S)-camphorsulfonic-10-acid, tartaric acid, in the presence of a solvent selected from the group consisting of: acetone, ethyl acetate and water.

23. A process according to claim 18, wherein a compound of formula (IV), (±)-(2-chlorophenyl)-(6,7-dihydro-4H-thieno[3,2-c]pyrid-5-yl)acetonitrile, in (±) or (−) or (+) forms are converted into a salt using a compound selected from the group consisting of: D-camphorsulfonate, L-camphor sulfonate, D-tartaric acid, L-tartaric acid and hydrogen sulfate.

24. A process according to claim 1 wherein the (−) isomer of a compound of formula (I) is racemized in a solvent using a base optionally selected from the group consisting of: LDA, NaOMe, NaH and KH.

25. A process according to claim 18 wherein the resolution of step (iii) is carried out in a solution comprising comprising acetone in the range of 5 to 10 volumes and water from 0% to 5%.

26. A process according to claim 18 wherein a suitable chiral agent is employed in a 1:1 molar ratio.

27. A process according to claim 26 wherein the process is carried out at a temperature of from 0° C. to the reflux temperature of the solvent.

28. A process according to claim 1 wherein the (−) form of a compound of formula (II) is racemized in a solvent using a base selected from the group consisting of: LDA, KOH, NaOH, K-t-BuOH, NaMe, NaH and KH.

* * * * *